(12) United States Patent
Kong et al.

(10) Patent No.: US 12,727,786 B2
(45) Date of Patent: Sep. 8, 2026

(54) NERVE STIMULATION (TENS) DEVICE

(71) Applicant: Neurometrix, Inc., Waltham, MA (US)

(72) Inventors: Xuan Kong, Acton, MA (US); Martin J. Moynihan, Waltham, MA (US); Shai N. Gozani, Brookline, MA (US)

(73) Assignee: Neurometrix, Inc., Waltham, MA (US)

( * ) Notice: Subject to any disclaimer, the term of this patent is extended or adjusted under 35 U.S.C. 154(b) by 149 days.

(21) Appl. No.: 15/811,219

(22) Filed: Nov. 13, 2017

(65) Prior Publication Data

US 2018/0132757 A1 May 17, 2018

Related U.S. Application Data

(60) Provisional application No. 62/420,728, filed on Nov. 11, 2016.

(51) Int. Cl.
*A61B 5/11* (2006.01)
*A61B 5/00* (2006.01)
(Continued)

(52) U.S. Cl.
CPC ............ *A61B 5/112* (2013.01); *A61B 5/1038* (2013.01); *A61B 5/1118* (2013.01); *A61B 5/4023* (2013.01); *A61B 5/6885* (2013.01); *A61N 1/0456* (2013.01); *A61N 1/36021* (2013.01); *A61B 5/6828* (2013.01); *A61B 2562/0219* (2013.01); *A61N 1/025* (2013.01);
(Continued)

(58) Field of Classification Search
CPC ..... A61B 5/681; A61B 5/6813; A61B 5/6824; A61B 5/6829; A61B 5/6831; A61B 5/112; A61B 5/1123; A61B 5/1038; A61B 5/4023; A61N 1/0456
See application file for complete search history.

(56) References Cited

U.S. PATENT DOCUMENTS 1,741,962 A 12/1929 Theodoropulos
4,290,431 A 9/1981 Herbert et al.
(Continued)

FOREIGN PATENT DOCUMENTS

CN 1665563 9/2005
CN 1919139 2/2007
(Continued)

OTHER PUBLICATIONS

U.S. Appl. No. 17/313,441 (Year: 2021).*
(Continued)

*Primary Examiner* — Carl H Layno
*Assistant Examiner* — Maria Catherine Anthony
(74) *Attorney, Agent, or Firm* — Farber LLC

(57) ABSTRACT

Apparatus for transcutaneous electrical nerve stimulation in a user, the apparatus comprising: a housing; an application unit for providing mechanical coupling between the housing and the user's body; a stimulation unit mounted to the housing for electrically stimulating at least one nerve with at least one stimulation pulse during a therapy session; and a determination unit mounted to the housing and configured to perform at least one of: (i) determining an activity level of the user; (ii) determining a gait characteristic of the user; (iii) determining a balance function of the user; and (iv) determining apparatus placement position on the user.

20 Claims, 12 Drawing Sheets

(51) Int. Cl.
*A61B 5/103* (2006.01)
*A61N 1/04* (2006.01)
*A61N 1/36* (2006.01)
*A61N 1/02* (2006.01)

(52) U.S. Cl.
CPC ........ *A61N 1/0484* (2013.01); *A61N 1/36031* (2017.08); *A61N 1/36034* (2017.08)

(56) References Cited

U.S. PATENT DOCUMENTS

D263,869 S 4/1982 Sumiyasu
4,503,863 A 3/1985 Katims
4,605,010 A 8/1986 McEwen
4,738,250 A 4/1988 Fulkerson et al.
4,777,711 A 10/1988 Forkner et al.
4,926,863 A 5/1990 Alt
4,989,605 A 2/1991 Rossen
5,048,523 A 9/1991 Yamasawa et al.
5,063,929 A 11/1991 Bartelt et al.
D323,561 S 1/1992 Bartelt et al.
5,121,747 A 6/1992 Andrews
5,169,384 A 12/1992 Bosniak et al.
D342,571 S 12/1993 Givens, Sr.
D346,029 S 4/1994 Shalvi
5,350,414 A 9/1994 Kolen
5,429,589 A 7/1995 Cartmell et al.
5,479,939 A 1/1996 Ogino
5,487,759 A 1/1996 Bastyr et al.
5,562,718 A 10/1996 Palermo
5,806,522 A 9/1998 Katims
D411,887 S 7/1999 Agarwala
5,919,149 A * 7/1999 Allum .................. A61B 5/4023 600/595
5,948,000 A 9/1999 Larsen et al.
5,954,758 A 9/1999 Peckham et al.
6,033,370 A 3/2000 Reinbold et al.
6,099,488 A 8/2000 Hung
6,132,387 A 10/2000 Gozani et al.
6,141,587 A 10/2000 Mower
6,148,233 A 11/2000 Owen et al.
6,161,044 A 12/2000 Silverstone
D443,362 S 6/2001 Storp
6,266,558 B1 7/2001 Gozani et al.
D450,313 S 11/2001 Koinuma
6,430,450 B1 8/2002 Bach-y-Rita et al.
D462,772 S 9/2002 Lamping et al.
6,456,884 B1 9/2002 Kenney
6,507,755 B1 1/2003 Gozani et al.
6,611,789 B1 * 8/2003 Darley ................. G04G 21/025 702/160
6,662,051 B1 12/2003 Eraker et al.
D484,984 S 1/2004 Takizawa et al.
D534,871 S 1/2007 Larsen
D541,042 S 4/2007 Andre et al.
D547,454 S 7/2007 Hsieh
D566,383 S 4/2008 Harris et al.
D584,414 S 1/2009 Lash et al.
D592,200 S 5/2009 Liu
D598,556 S 8/2009 Chen
D600,352 S 9/2009 Cryan
D607,198 S 1/2010 Andre et al.
D609,353 S 2/2010 Cryan
7,668,598 B2 2/2010 Herregraven et al.
D611,611 S 3/2010 Sachi et al.
D615,526 S 5/2010 Andre et al.
7,720,548 B2 5/2010 King
7,725,193 B1 5/2010 Chu
7,787,946 B2 8/2010 Stahmann et al.
D625,016 S 10/2010 Potts et al.
D625,829 S 10/2010 Arbesman et al.
D629,115 S 12/2010 Robertson
7,887,493 B2 2/2011 Stahmann et al.
D636,881 S 4/2011 Clemens et al.
D637,988 S 5/2011 Jinkinson
8,108,049 B2 1/2012 King
8,121,702 B2 2/2012 King
8,131,374 B2 3/2012 Moore et al.
D658,302 S 4/2012 Nixon
8,284,070 B2 10/2012 Chaudhari et al.
D677,792 S 3/2013 Vandiver
D680,735 S 4/2013 Itabashi et al.
8,421,642 B1 4/2013 McIntosh et al.
D687,951 S 8/2013 Della Torre et al.
D688,707 S 8/2013 Vincent et al.
D704,848 S 5/2014 Thomas et al.
D705,428 S 5/2014 Cheney et al.
D712,045 S 8/2014 Thornton
D712,052 S 8/2014 Thomas et al.
D713,049 S 9/2014 Shah
8,825,175 B2 9/2014 King
8,849,407 B1 9/2014 Danilov et al.
D716,457 S 10/2014 Brefka et al.
8,862,238 B2 10/2014 Rahimi et al.
D716,963 S 11/2014 Yosef et al.
8,948,876 B2 2/2015 Gozani et al.
D732,682 S 6/2015 Porat
D735,873 S 8/2015 Brefka et al.
9,168,375 B2 10/2015 Rahimi et al.
9,173,581 B2 11/2015 Boettcher et al.
D744,661 S 12/2015 Rizzi
D745,975 S 12/2015 Igaue et al.
D750,263 S 2/2016 Shigeno et al.
D750,798 S 3/2016 Yosef et al.
9,282,287 B1 3/2016 Marsh
9,282,897 B2 3/2016 Ross, Jr. et al.
D754,355 S 4/2016 Ganapathy et al.
D754,973 S 5/2016 Danze et al.
D757,292 S 5/2016 Chen
D758,605 S 6/2016 Chen
D758,606 S 6/2016 Chen
D759,262 S 6/2016 Chen
D759,263 S 6/2016 Chen
D759,958 S 6/2016 Requa
D762,628 S 8/2016 Yoon et al.
D762,872 S 8/2016 Chen
D767,775 S 9/2016 Gilmer et al.
9,452,287 B2 9/2016 Rosenbluth et al.
9,474,898 B2 10/2016 Gozani et al.
D774,654 S 12/2016 Anderson
D775,361 S 12/2016 Vosch et al.
D778,453 S 2/2017 Knaus et al.
D779,677 S 2/2017 Chen
9,561,397 B2 2/2017 Zaki
D784,544 S 4/2017 Dudkiewicz et al.
D784,546 S 4/2017 Gordon
D784,946 S 4/2017 Jun et al.
D788,056 S 5/2017 Choi et al.
9,656,070 B2 5/2017 Gozani et al.
D789,546 S 6/2017 Matfus et al.
D789,547 S 6/2017 Matfus et al.
D791,333 S 7/2017 Wilson
D792,363 S 7/2017 Kim et al.
9,700,724 B2 7/2017 Liu et al.
D794,331 S 8/2017 Grote
9,731,126 B2 * 8/2017 Ferree ...................... A61B 5/11
D798,170 S 9/2017 Toth et al.
D801,542 S 10/2017 Anderson
D802,780 S 11/2017 Hsu
9,827,420 B2 11/2017 Ferree et al.
D806,669 S 1/2018 Kangasmaa et al.
D810,311 S 2/2018 Chen
D810,843 S 2/2018 Karvandi
D810,952 S 2/2018 Hsu
D811,729 S 3/2018 Bysshe
D813,405 S 3/2018 Ho
D813,407 S 3/2018 Chen
D813,408 S 3/2018 Chen
D821,592 S 6/2018 Pham et al.
D828,569 S 9/2018 Mercuro
D829,182 S 9/2018 Li
10,076,662 B2 9/2018 Tuan
D830,565 S 10/2018 Xu
D831,017 S 10/2018 Choe et al.

(56) References Cited

U.S. PATENT DOCUMENTS

D831,221 S 10/2018 Smith
D831,335 S 10/2018 Crease
D832,230 S 10/2018 Lee et al.
D834,719 S 11/2018 Theriot et al.
D836,788 S 12/2018 Peng
10,154,922 B1 12/2018 Perez et al.
D837,394 S 1/2019 Cryan et al.
10,279,179 B2 5/2019 Gozani
10,335,595 B2 7/2019 Ferree et al.
D857,910 S 8/2019 Cryan et al.
D861,903 S 10/2019 Cryan et al.
D861,904 S 10/2019 Ho
D862,716 S 10/2019 Cryan et al.
D865,986 S 11/2019 Cryan et al.
D879,983 S 3/2020 Wang
10,940,311 B2 3/2021 Gozani et al.
11,247,040 B2* 2/2022 Ferree ................ A61N 1/36031
2002/0010497 A1 1/2002 Merfeld et al.
2003/0023192 A1 1/2003 Foxlin
2003/0074037 A1 4/2003 Moore et al.
2003/0114892 A1 6/2003 Nathan et al.
2003/0208246 A1 11/2003 Kotlik et al.
2004/0049241 A1 3/2004 Campos
2004/0122483 A1 6/2004 Nathan et al.
2004/0173220 A1 9/2004 Harry et al.
2005/0059903 A1 3/2005 Izumi
2005/0080463 A1 4/2005 Stahmann et al.
2005/0097970 A1 5/2005 Nurse
2005/0131317 A1 6/2005 Oddsson et al.
2005/0234525 A1 10/2005 Phillips
2005/0283204 A1 12/2005 Buhlmann et al.
2006/0052788 A1 3/2006 Thelen et al.
2006/0064037 A1 3/2006 Shalon et al.
2006/0085047 A1 4/2006 Unsworth et al.
2006/0085049 A1 4/2006 Cory et al.
2006/0089683 A1 4/2006 Hagglof et al.
2006/0095088 A1 5/2006 De Ridder
2006/0173507 A1 8/2006 Mrva et al.
2006/0190057 A1 8/2006 Reese
2006/0251334 A1 11/2006 Oba et al.
2007/0021786 A1 1/2007 Parnis et al.
2007/0060922 A1 3/2007 Dreyfuss
2007/0203435 A1 8/2007 Novak
2007/0203547 A1 8/2007 Costello et al.
2007/0276449 A1 11/2007 Gunter et al.
2008/0009772 A1* 1/2008 Tyler ...................... G06F 3/015
600/595
2008/0077192 A1 3/2008 Harry et al.
2008/0146980 A1 6/2008 Rousso et al.
2008/0147143 A1 6/2008 Popovic et al.
2008/0147146 A1 6/2008 Wahlgren et al.
2008/0172102 A1 7/2008 Shalev
2008/0312709 A1 12/2008 Volpe et al.
2009/0030476 A1 1/2009 Hargrove
2009/0076364 A1 3/2009 Libbus et al.
2009/0082829 A1 3/2009 Panken et al.
2009/0082831 A1 3/2009 Paul et al.
2009/0112214 A1 4/2009 Philippon et al.
2009/0131993 A1 5/2009 Rousso et al.
2009/0203972 A1 8/2009 Heneghan et al.
2009/0240303 A1 9/2009 Wahlstrand et al.
2009/0264789 A1 10/2009 Molnar et al.
2009/0270947 A1 10/2009 Stone et al.
2009/0326604 A1 12/2009 Tyler et al.
2010/0004715 A1 1/2010 Fahey
2010/0010585 A1 1/2010 Davis et al.
2010/0042180 A1 2/2010 Mueller et al.
2010/0057149 A1 3/2010 Fahey
2010/0087903 A1 4/2010 Van Herk et al.
2010/0094103 A1 4/2010 Kaplan et al.
2010/0114257 A1 5/2010 Torgerson
2010/0131028 A1 5/2010 Hsu et al.
2010/0198124 A1 8/2010 Bhugra
2010/0217349 A1 8/2010 Fahey
2010/0241464 A1 9/2010 Amigo et al.
2010/0274304 A1* 10/2010 Wang .................. A61B 5/6887
600/595
2011/0066209 A1 3/2011 Bodlaender et al.
2011/0106213 A1 5/2011 Davis et al.
2011/0166622 A1 7/2011 Crosson et al.
2011/0190594 A1 8/2011 Heit et al.
2011/0224665 A1 9/2011 Crosby et al.
2011/0245711 A1 10/2011 Katra et al.
2011/0257468 A1 10/2011 Oser et al.
2011/0264171 A1 10/2011 Torgerson
2011/0276107 A1 11/2011 Simon et al.
2011/0282164 A1 11/2011 Yang et al.
2012/0010680 A1 1/2012 Wei et al.
2012/0108998 A1 5/2012 Molnar et al.
2012/0123227 A1 5/2012 Sun et al.
2012/0130449 A1 5/2012 Carlyon et al.
2012/0303077 A1 11/2012 De Vincentiis
2012/0319816 A1 12/2012 Al-Ali
2013/0079846 A1 3/2013 Single
2013/0096641 A1 4/2013 Strother et al.
2013/0116514 A1* 5/2013 Kroner ................. A61B 5/4094
600/301
2013/0158627 A1 6/2013 Gozani et al.
2013/0197341 A1 8/2013 Grob et al.
2013/0217998 A1 8/2013 Mahfouz et al.
2013/0317333 A1 11/2013 Yang et al.
2014/0005759 A1 1/2014 Fahey et al.
2014/0039450 A1 2/2014 Green et al.
2014/0057232 A1 2/2014 Wetmore et al.
2014/0081353 A1 3/2014 Cook et al.
2014/0088192 A1 3/2014 Heller et al.
2014/0107729 A1 4/2014 Sumners et al.
2014/0163444 A1 6/2014 Ingvarsson et al.
2014/0188194 A1 7/2014 Schepis et al.
2014/0206976 A1 7/2014 Thompson et al.
2014/0221797 A1 8/2014 Bailey et al.
2014/0245784 A1 9/2014 Proud et al.
2014/0245791 A1 9/2014 Proud et al.
2014/0276236 A1* 9/2014 Swain ................. A61B 5/1038
600/592
2014/0276549 A1 9/2014 Osorio
2014/0296934 A1 10/2014 Gozani et al.
2014/0296935 A1 10/2014 Ferree et al.
2014/0309709 A1* 10/2014 Gozani ............. A61N 1/36021
607/46
2014/0336725 A1 11/2014 Nogueira
2014/0336730 A1 11/2014 Simon et al.
2014/0343625 A1 11/2014 O Laighin
2014/0371547 A1 12/2014 Gartenberg et al.
2014/0371814 A1* 12/2014 Spizzirri ............. A61N 1/0492
607/48
2014/0379045 A1 12/2014 Rahimi et al.
2015/0012068 A1 1/2015 Bradley et al.
2015/0045853 A1 2/2015 Alataris et al.
2015/0100107 A1 4/2015 Kiani et al.
2015/0157242 A1 6/2015 Sabesan
2015/0157868 A1 6/2015 Franke et al.
2015/0174402 A1 6/2015 Thomas et al.
2015/0238094 A1 8/2015 Lai et al.
2015/0272511 A1* 10/2015 Najafi ................. A61B 5/7275
600/595
2015/0306387 A1 10/2015 Kong et al.
2015/0321000 A1 11/2015 Rosenbluth et al.
2015/0328467 A1 11/2015 Demers et al.
2015/0335288 A1 11/2015 Toth et al.
2015/0335877 A1 11/2015 Jeffery et al.
2016/0007931 A1 1/2016 Rubin et al.
2016/0029891 A1 2/2016 Lin
2016/0113551 A1* 4/2016 Annegarn ............. A61B 5/742
600/595
2016/0144174 A1* 5/2016 Ferree .................. A61B 5/1116
600/595
2016/0151628 A1 6/2016 Simon et al.
2016/0166198 A1 6/2016 Oddsson et al.
2016/0189371 A1* 6/2016 Krishna Rao ......... G06T 7/0012
382/128
2016/0213924 A1 7/2016 Coleman et al.
2016/0235981 A1 8/2016 Southwell et al.

(56) References Cited

U.S. PATENT DOCUMENTS

| | | | | |
|---|---|---|---|---|
| 2016/0242646 | A1* | 8/2016 | Obma | A61B 5/01 |
| 2016/0243359 | A1 | 8/2016 | Sharma | |
| 2016/0250464 | A1 | 9/2016 | Zschaeck et al. | |
| 2016/0310730 | A1 | 10/2016 | Martins et al. | |
| 2016/0367823 | A1 | 12/2016 | Cowan et al. | |
| 2017/0043160 | A1 | 2/2017 | Goodall et al. | |
| 2017/0056650 | A1 | 3/2017 | Cohen et al. | |
| 2017/0080207 | A1 | 3/2017 | Perez et al. | |
| 2017/0095670 | A1* | 4/2017 | Ghaffari | A61M 21/02 |
| 2017/0188864 | A1 | 7/2017 | Drury | |
| 2017/0188872 | A1 | 7/2017 | Hughes et al. | |
| 2017/0209693 | A1 | 7/2017 | An et al. | |
| 2017/0224990 | A1 | 8/2017 | Goldwasser et al. | |
| 2017/0238812 | A1 | 8/2017 | Atlas | |
| 2017/0368345 | A1 | 12/2017 | Kong et al. | |
| 2018/0000685 | A1 | 1/2018 | Maloney et al. | |
| 2018/0028808 | A1 | 2/2018 | Ferree et al. | |
| 2018/0177996 | A1 | 6/2018 | Gozani et al. | |
| 2018/0345014 | A1 | 12/2018 | Gozani et al. | |
| 2019/0001135 | A1 | 1/2019 | Yoo et al. | |
| 2019/0022372 | A1 | 1/2019 | Dar et al. | |
| 2019/0022386 | A1 | 1/2019 | Gozani et al. | |
| 2019/0134393 | A1 | 5/2019 | Wong et al. | |
| 2020/0179694 | A1 | 6/2020 | Kong et al. | |
| 2020/0219615 | A1 | 7/2020 | Rabin et al. | |
| 2021/0128904 | A1 | 5/2021 | Terekhov | |
| 2021/0260374 | A1 | 8/2021 | Gozani et al. | |

FOREIGN PATENT DOCUMENTS

| | | | |
|---|---|---|---|
| CN | 1926496 | 3/2007 | |
| CN | 101557788 | 10/2009 | |
| CN | 101626804 | 1/2010 | |
| CN | 102202131 | 9/2011 | |
| CN | 102355847 | 2/2012 | |
| CN | 102740919 | 10/2012 | |
| DE | 102010052710 | 5/2012 | |
| EP | 0971653 | 1/2000 | |
| EP | 1985277 | 2/2015 | |
| JP | 61-171943 | 10/1986 | |
| JP | 4-347140 | 12/1992 | |
| JP | 9-117453 | 5/1997 | |
| JP | 2000-167067 | 6/2000 | |
| JP | 2005-34402 | 2/2005 | |
| JP | 2005-81068 | 3/2005 | |
| JP | 2006-68300 | 3/2006 | |
| JP | 4185846 | 9/2008 | |
| WO | WO 97/42999 | 11/1997 | |
| WO | WO 99/64105 | 12/1999 | |
| WO | WO 03/051453 | 6/2003 | |
| WO | WO 2004/078132 | 9/2004 | |
| WO | WO 2007/061746 | 5/2007 | |
| WO | WO 2008/079757 | 7/2008 | |
| WO | WO 2008/088985 | 7/2008 | |
| WO | WO 2009/036313 | 3/2009 | |
| WO | WO 2011/075179 | 6/2011 | |
| WO | WO 2011/137193 | 11/2011 | |
| WO | WO 2012/116407 | 9/2012 | |
| WO | WO 2013/028960 | 2/2013 | |
| WO | WO 2014/172381 | 10/2014 | |
| WO | WO 2015/123373 | 8/2015 | |
| WO | WO-2015123373 A1 * | 8/2015 | A61B 5/0004 |
| WO | WO 2016/201366 | 12/2016 | |
| WO | WO 2018/089655 | 5/2018 | |
| WO | WO 2020/033883 | 2/2020 | |

OTHER PUBLICATIONS

Hausdorff. Jeffrey M. et al., Gait Variability and Fall Risk in Community-Living Older Adults: A 1-Year Prospective Study, Arch Phys Med Rehabil, Aug. 2001, vol. 82, pp. 1050-1056.

Amazon, "Quell 2.0 Wearable Pain Relief Technology", Sep. 15, 2018.http://www.amazon/com/Quell-Wearable-Pain-Relief-Technology/dp/B07DHW2MJJ/ref=cm_cr_arp_d_product_top? ie=UTF8. Shown on p. 1. (Year: 2018).

Amazon, "Quell Wearable Pain Relief Technology Starter Kit", Oct. 18, 2017. http://www.amazon.com/Quell-Wearable-ReliefTechnology-Starter/dp/B075YVCLZT/ref=cm_cr_arp_d_product_top?ie=UTF8. Shown on p. 1. (Year: 2017).

Ancoli-Israel, S. et al., The Role of Actigraphy in the Study of Sleep and Circadian Rhythms, Sleep, 2003, 26(3), p. 342-392.

Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 8, p. 1039-1062.

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Bjordal JM et al., Transcutaneous electrical nerve stimulation (TENS) can reduce postoperative analgesic consumption. A meta-analysis with assessment of optimal treatment parameters for post-operative pain, European Journal of Pain, 2003, vol. 7(2): 181-188.

Bloodworth Dm et al., Comparison of stochastic vs. conventional transcutaneous electrical stimulation for pain modulation in patients with electromyographically documented radiculopathy, American Journal of Physical Medicine & Rehabilitation, 2004, vol. 83(8): 584-591.

Bonnet, M. et al., Recording and Scoring Leg Movements, Sleep, 1993, vol. 16, No. 8, p. 748-759.

Boyle, J. et al., Randomized, Placebo-Controlled Comparison of Amitriptyline, Duloxetine, and Pregabalin in Patients With Chronic Diabetic Peripheral Neuropathic Pain, Diabetes Care, 2012, vol. 35, p. 2451-2458.

Chandran P et al., Development of opioid tolerance with repeated transcutaneous electrical nerve stimulation administration, Pain, 2003, vol. 102: 195-201.

Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.

Chen CC et al., An investigation into the effects of frequency-modulated transcutaneous electrical nerve stimulation (TENS) on experimentally-induced pressure pain in healthy human participants, The Journal of Pain, 2009, vol. 10(10): 1029-1037.

Chen CC et al., Differential frequency effects of strong nonpainful transcutaneous electrical nerve stimulation on experimentally induced ischemic pain in healthy human participants, The Clinical Journal of Pain, 2011, vol. 27(5): 434-441.

Chen CC et al., Does the pulse frequency of transcutaneous electrical nerve stimulation (TENS) influence hypoalgesia? A systematic review of studies using experimantal pain and healthy human participants, Physiotherapy, 2008, vol. 94: 11-20.

Claydon LS et al., Dose-specific effects of transcutaneous electrical nerve stimulation on experimental pain, Clinical Journal of Pain, 2011, vol. 27(7): 635-647.

Cole, R.J. et al., Automatic Sleep/Wake Identification From Wrist Activity, Sleep, 1992, 15(5), p. 461-469.

Cruccu G. et al., EFNS guidelines on neurostimulation therapy for neuropathic pain, European Journal of Neurology, 2007, vol. 14: 952-970.

Davies HTO et al., Diminishing returns or appropriate treatment strategy?—an analysis of short-term outcomes after pain clinic treatment, Pain, 1997, vol. 70: 203-208.

Desantana JM et al., Effectiveness of transcutaneous electrical nerve stimulation for treatment of hyperalgesia and pain, Curr Rheumatol Rep. 2008, vol. 10(6): 492-499.

Dubinsky RM et al., Assessment: Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74: 173-176.

Fary RE et al., Monophasic electrical stimulation produces high rates of adverse skin reactions in healthy subjects, Physiotherapy Theory and Practice, 2011, vol. 27(3): 246-251.

Fishbain, David A. et al. Does Pain Mediate the Pain Interference with Sleep Problem in Chronic Pain? Findings from Studies for

(56) References Cited

OTHER PUBLICATIONS

Management of Diabetic Peripheral Neuropathic Pain with Duloxetine, Journal of Pain Symptom Management, Dec. 2008; 36(6):639-647.
Fishbain, David A. et al., Transcutaneous Electrical Nerve Stimulation (TENS) Treatment Outcome in Long-Term Users, The Clinical Journal of Pain, Sep. 1996; 12(3):201-214.
Food and Drug Administration, Draft Guidance for Industry and Staff: Class II Special Controls Guidance Document: Transcutaneous Electrical Nerve Stimulator for Pain Relief, Apr. 5, 2010.
Garrison DW et al., Decreased activity of spontaneous and noxiously evoked dorsal horn cells during transcutaneous electrical nerve stimulation (TENS), Pain, 1994, vol. 58: 309-315.
Gilron, I. et al., Chronobiological Characteristics of Neuropathic Pain: Clinical Predictors of Diurnal Pain Rhythmicity, The Clinical Journal Of Pain, 2013.
Hori, T. et al., Skin Potential Activities And Their Regional Differences During Normal Sleep In Humans, The Japanese Journal of Physiology, 1970, vol. 20, p. 657-671.
Jelinek HF et al., Electric pulse frequency and magnitude of perceived sensation during electrocutaneous forearm stimulation, Arch Phys Med Rehabil, 2010, vol. 91: 1372-1382.
Jin DM et al., Effect of transcutaneous electrical nerve stimulation on symptomatic diabetic peripheral neuropathy: a meta-analysis of randomized controlled trials, Diabetes Research and Clinical Practice, 2010, vol. 89: 10-15.
Johnson MI et al., Analgesic effects of different frequencies of transcutaneous electrical nerve stimulation on cold-induced pain in normal subjects, Pain, 1989, vol. 39: 231-236.
Johnson MI et al., Transcutaneous Electrical Nerve Stimulation (TENS) and TENS-like devices: do they provide pain relief?, Pain Reviews, 2001, vol. 8: 7-44.
Johnson MI et al., Transcutaneous electrical nerve stimulation for the management of painful conditions: focus on neuropathic pain, Expert Review of Neurotherapeutics, 2011, vol. 11(5): 735-753.
Johnson, M.I. et al., An in-depth study of long-term users of transcutaneous electrical nerve stimulation (TENS). Implications for clinical use of TENS. Pain. Mar. 1991;44(3):221-229.
Kaczmarek, Kurt A. et al.. Electrotactile and Vibrotactile Displays for Sensory Substitution Systems. IEEE Trans. Biomed. Eng. Jan. 1991;38 (1):1-16.
Kantor G et al., The effects of selected stimulus waveforms on pulse and phase characteristics at sensory and motor thresholds, Physical Therapy, 1994, vol. 74(10): 951-962.
Keller, Thierry et al., Electrodes for transcutaneous (surface) electrical stimulation. J. Automatic Control, University of Belgrade. 2008; 18(2):35-45.
Koumans, A. J. R. et al., Electrodermal Levels And Fluctuations During Normal Sleep, Psychophysiology, 1968, 5(3), p. 300-306.
Kovacevic-Ristanovic, R. et al., Nonpharmacologic Treatment of Periodic Leg Movements in Sleep, Arch. Phys. Med. Rehabil., 1991, vol. 72, p. 385-389.
Kripke, D.F. et al., Wrist Actigraphic Scoring for Sleep Laboratory Patients: Algorithm Development, Journal of Sleep Research, 2010, 19(4), p. 612-619.
Law PPW et al., Optimal stimulation frequency of transcutaneous electrical nerve stimulation on people with knee osteoarthritis, J Rehabil Med, 2004, vol. 36: 220-225.
Leonard G et al., Deciphering the role of endogenous opioids in high-frequency TENS using low and high doses of naloxone, Pain, 2010, vol. 151: 215-219.
Levy et al., A comparison of two methods for measuring thermal thresholds in diabetic neuropathy, Journal of Neurology, Neurosurgery, and Psychiatry, 1989, vol. 52: 1072-1077.
Lopes, L. et al., Restless Legs Syndrome and Quality of Sleep in Type 2 Diabetes, Diabetes Care, 2005, vol. 28, No. 11, p. 2633-2636.
Lykken, D.T., Properties of Electrodes Used in Electrodermal Measurement. J. Comp. Physiol. Psychol. Oct. 1959; 52:629-634.
Lykken, D.T., Square-Wave Analysis of Skin Impedance. Psychophysiology. Sep. 1970; 7(2):262-275.
MacFarlane, T. et al., Whether the weather influences pain? Results from EpiFunD study in North West England, Rheumatology, 2010, vol. 49, pp. 1513-1520.
Melzack R et al., Pain mechanisms: A New Theory, Science, 1965, vol. 150(3699): 971-979.
Moran F et al., Hypoalgesia in response to transcutaneous electrical nerve stimulation (TENS) depends on stimulation intensity, The Journal of Pain, 2011, vol. 12(8): 929-935.
Nightingale, S., The neuropathic pain market, Nature Reviews, 2012, vol. 11, p. 101-102.
Okamoto-Mizuno. K. et al., Effects of thermal environment on sleep and circadlan rhythm, Journal of Physiological Anthropology, 2012, vol. 31, No. 14, pp. 1-9.
Oosterhof, Jan et al., Outcome of transcutaneous electrical nerve stimulation in chronic pain: short-term results of a double-blind, randomised, placebo-controlled trial. J. Headache Pain. Sep. 2006; 7 (4):196-205.
Oosterhof, Jan et al., The long-term outcome of transcutaneous electrical nerve stimulation in the treatment for patients with chronic pain: a randomized, placebo-controlled trial. Pain Pract. Sep. 2012; 12(7):513-522.
Pantaleao MA et al., Adjusting pulse amplitude during transcutaneous electrical nerve stimulation (TENS) application produces greater hypoalgesia, The Journal of Pain, 2011, vol. 12(5): 581-590.
Paquet, J. et al., Wake Detection Capacity of Actigraphy During Sleep, Sleep, 2007, 30(10), p. 1362-1369.
Pieber K et al., Electrotherapy for the treatment of painful diabetic peripheral neuropathy: a review, Journal of Rehabilitation Medicine, 2010, vol. 42: 289-295.
Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.
Sadeh, A., The Role and Validity of Actigraphy in Sleep Medicine: An Update, Sleep Medicine Reviews, 2011, vol. 15, p. 259-267.
Sadosky, A. et al., Burden of Illness Associated with Painful Diabetic Peripheral Neuropathy Among Adults Seeking Treatment in the US: Results from a Retrospective Chart Review and Cross-Sectional Survey, Diabetes, Metabolic Syndrome and Obesity: Targets and Therapy, 2013, vol. 6, p. 79-92.
Sano, A et al, Quantitative analysis of wrist electrodermal activity during sleep, International Journal of Psychophysiology, 2014, vol. 94, pp. 382-389.
Scherder, E. J. A. et al., Transcutaneous Electrical Nerve Stimulation (TENS) Improves the Rest-Activity Rhythm in Midstage Alzheimer's Disease, Behavioral Brain Research, 1999, vol. 101, p. 105-107.
Sheridan et al., Some Factors Influencing the Threshold of the Electrocutaneous Stimulus, Perceptual and Motor Skills, 1966, vol. 22, pp. 647-654.
Susi et al., Motion Mode Recognition and Step Detection Algorithms for Mobile Phone Users, Sensors, Jan. 24, 2013, vol. 13, pp. 1539-1562.
Timmermans, E. et al., Self-perceived weather sensitivity and joint pain in older people with osteoarthritis in six European countries: results from the European Project on OSteoArthritis (EPOSA), BMC Musculoskeletal Disorders, 2014, vol. 15, No. 66, pp. 1-11.
Tryon, W. W., Issues of Validity in Actigraphic Sleep Assessment, Sleep, 2004, 27(1), p. 158-165.
Tsai, Y. et al., Impact of Subjective Sleep Quality on Glycemic Control in Type 2 Diabetes Mellitus, Family Practice, 2012, vol. 29, p. 30-35.
Van Boxtel, A., Skin resistance during square-wave electrical pulses of 1 to 10 mA. Med. Biol. Eng. Comput. Nov. 1977; 15(6):679-687.
Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.
Waeber, R. et al., Biosection Search with Noisy Responses, SIAM J. Control Optim., 2013, vol. 51, No. 3, pp. 2261-2279.
Webster, J. B. et al., An Activity-Based Sleep Monitor System for Ambulatory Use, Sleep, 1982, 5(4), p. 389-399.

(56) References Cited

OTHER PUBLICATIONS

Zelman, D. C. et al., Sleep Impairment in Patients With Painful Diabetic Peripheral Neuropathy, The Clinical Journal Of Pain, 2006, 22(8), p. 681-685.

Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.

Dailey, D. et al., Transcutaneous Electrical Nerve Stimulation Reduces Movement-Evoked Pain and Fatigue: A Randomized, Controlled Trial, Arthritis & Rheumatology, May 2020, vol. 72, No. 5, pp. 824-836.

Bifulco, P. et al., A Stretchable, Conductive Rubber Sensor to Detect Muscle Contraction for Prosthetic Hand Control, The 6th IEEE international Conference on E-Health and Bioengineering—EHB 2017, Jun. 22-24, 2017, pp. 173-176.

AMFT, O. et al., Sensing Muscle Activities with Body-Worn Sensors, Conference Paper, May 2006.

Gozani SN et al., Fixed-Site High-Frequency Transcutaneous Electrical Nerve Stimulation for Treatment of Chronic Low Back and Lower Extremity Pain, Journal of Pain Research, 2016, vol. 9, pp. 469-479.

Ossipov MH et al., Central Modulation of Pain, The Journal of Clinical Investigation, Nov. 2010, vol. 120, No. 11, pp. 3779-3787.

Dailey DL et al., Transcutaneous Electrical Nerve Stimulation (TENS) Reduces Pain, Fatigue, and Hyperalgesia while Restoring Central Inhibition in Primary Fibromyalgia, Pain, Nov. 2013, vol. 154, No. 11, pp. 2554-2562.

Taborri et al., A Novel HMM Distributed Classifier for the Detection of Gait Phases by Means of a Wearable Inertial Sensor Network, Sensors, Sep. 2014, vol. 14, pp. 16212-16234.

Vance et al., Using TENS for pain control: the state of the evidence, Pain Management, 2014, vol. 4, No. 3, pp. 197-209.

Mallik et al., Nerve Conduction Studies: Essentials and Pitfalls in Practice, Neurol Neurosurg Psychiatry, 2005, ii23-ii31.

* cited by examiner

NERVE STIMULATION (TENS) DEVICE

REFERENCE TO PENDING PRIOR PATENT APPLICATION

This patent application claims benefit of prior U.S. Provisional Patent Application Ser. No. 62/420,728, filed Nov. 11, 2016 by NeuroMetrix, Inc. and Xuan Kong for APPARATUS AND METHODS FOR ACTIVITY MONITORING, GAIT ANALYSIS, AND BALANCE ASSESSMENT OF USERS OF A TRANSCUTANEOUS ELECTRICAL NERVE STIMULATION DEVICE, which patent application is hereby incorporated herein by reference.

FIELD OF THE INVENTION

This invention relates generally to Transcutaneous Electrical Nerve Stimulation (TENS) devices that deliver electrical currents across the intact skin of a user via electrodes to provide symptomatic relief of pain. More specifically, this invention relates to apparatus and methods for analyzing gait characteristics, monitoring activity levels, assessing balance functions, and determining device placement positions based on motion-tracking sensor data such as that provided by an accelerometer incorporated within the TENS device. One or more aspects of gait, activity level, balance and device placement assessment may also be used to modify the operation of the TENS device.

BACKGROUND OF THE INVENTION

Transcutaneous electrical nerve stimulation (TENS) is the delivery of electricity (i.e., electrical stimulation) across the intact surface of a user's skin in order to activate sensory nerve fibers. The most common application of TENS therapy is to provide analgesia, such as for alleviation of chronic pain. Other applications of TENS therapy include, but are not limited to, reducing the symptoms of restless leg syndrome, decreasing nocturnal muscle cramps, and providing relief from generalized pruritus.

People suffering from chronic pain often have a reduced level of activity, unsteady gait, and poor balance. A sedentary lifestyle can lead to a worsening of pain. Unstable gait and poor balance is predictive of falls. The side effects of certain pain medications can also lead to a reduced activity level, unsteady gait, and poor balance.

A conceptual model for how sensory nerve stimulation leads to pain relief was proposed by Melzack and Wall in 1965. Their theory proposes that the activation of sensory nerves (Aβ fibers) closes a "pain gate" in the spinal cord that inhibits the transmission of pain signals carried by nociceptive afferents (C and Aδ fibers) to the brain. In the past 20 years, anatomic pathways and molecular mechanisms that may underlie the pain gate have been identified. Sensory nerve stimulation (e.g., via TENS) activates the descending pain inhibition system, primarily the periaqueductal gray (PAG) and rostroventral medial medulla (RVM) located in the midbrain and medulla sections of the brainstem, respectively. The PAG has neural projections to the RVM, which in turn has diffuse bilateral projections into the spinal cord dorsal horn that inhibit ascending pain signal transmission.

TENS is typically delivered in short discrete pulses, with each pulse typically being several hundred microseconds in duration, at frequencies between about 10 and 150 Hz, through hydrogel electrodes placed on the user's body. TENS is characterized by a number of electrical parameters including the amplitude and shape of the stimulation pulse (which combine to establish the pulse charge), the frequency and pattern of the pulses, the duration of a therapy session, and the interval between therapy sessions. All of these parameters are correlated to the therapeutic dose. For example, higher amplitude and longer pulses (i.e., larger pulse charge) increase the dose, whereas shorter therapy sessions decrease the dose. Clinical studies suggest that pulse charge and therapy session duration have the greatest impact on therapeutic dose.

To achieve maximum pain relief (i.e., hypoalgesia), TENS needs to be delivered at an adequate stimulation intensity. Intensities below the threshold of sensation are not clinically effective. The optimal therapeutic intensity is often described as one that is "strong yet comfortable". Most TENS devices rely on the user to set the stimulation intensity, usually through a manual intensity control comprising an analog intensity knob or digital intensity control push-buttons. In either case (i.e., analog control or digital control), the user must manually increase the intensity of the stimulation to a level that the user believes to be a therapeutic level. Therefore, a major limitation of current TENS devices is that it may be difficult for many users to determine an appropriate therapeutic stimulation intensity. As a result, the user may either require substantial support from medical staff or they may fail to get pain relief due to an inadequate stimulation level.

A newly-developed wearable TENS device (i.e., Quell®, Neurometrix, Inc., Waltham, Ma., USA) uses a novel method for calibrating the stimulation intensity in order to maximize the probability that the TENS stimulation intensity will fall within the therapeutic range. With the Quell® device, the user identifies their electrotactile sensation threshold and then the therapeutic intensity is automatically estimated by the TENS device based on the identified electrotactile sensation threshold.

Pain relief from TENS stimulation usually begins within 15 minutes of the stimulation onset and may last up to an hour following the completion of the stimulation period (which is also known as a "therapy session"). Each therapy session typically runs for 30-60 minutes. To maintain maximum pain relief (i.e., hypoalgesia), TENS therapy sessions typically need to be initiated at regular intervals. Newly-developed wearable TENS devices, such as the aforementioned Quell® device, provide the user with an option to automatically restart therapy sessions at pre-determined time intervals.

Assessments of the therapeutic benefits of TENS therapy are often subjective, infrequent, and incomplete, such as those measured by responses to clinical questionnaires or pain diaries. Furthermore, the perception of pain (i.e., the subject's self-evaluation of pain levels) is only one of many important aspects of effective pain relief. A more active lifestyle, steadier gait, and better balance are important examples of an improved quality of life and health. These improvements can be attributed to a reduction of pain as a result of TENS therapy. The same level of pain relief can also be achieved with a reduced intake of pain medication coupled with TENS therapy. A reduction in the use of pain medication may mitigate the side effects of pain medications and lead to a better quality of life and improved health, such as an increase in activity levels, a reduction in gait variability, and an improvement in balance.

Over time, a preferred TENS therapy dose may differ, depending upon perceived pain levels and the interference of pain on quality of life and health metrics. The perceived pain and interference levels may change with the progression of pain relief after a period of TENS therapy. TENS therapy dose adjustment is often lacking or arbitrary in the absence of an objective and real-time assessment of the impact of TENS therapy. To maintain a stable and uniform therapeutic effectiveness of TENS therapy for a particular user, objective and measurable biomarkers (e.g., activity levels, gait stability, and ability to maintain balance) can be utilized. By monitoring activity, gait, and balance continuously and objectively, a TENS therapy dose may be further optimized for each individual user.

SUMMARY OF THE INVENTION

The present invention comprises the provision and use of a novel TENS device which comprises a stimulator designed to be placed on a user's upper calf (or other anatomical location) and a pre-configured electrode array designed to provide electrical stimulation to at least one nerve disposed in the user's upper calf (or other anatomical location). A three-axis accelerometer incorporated into the TENS device measures the motion and orientation of the user's lower limb in order to continuously and objectively measure activity, gait, and balance. A key feature of the present invention is that the novel TENS device automatically adjusts its stimulation parameters according to the aforementioned activity, gait, and balance measurements in order to reduce pain and in order to minimize the interference of pain with one or more aspects of quality of life. Another key feature of the present invention is that the novel TENS device automatically determines the limb upon which the device is placed and the rotational position of the device on the upper calf of the user.

In one preferred form of the invention, there is provided apparatus for transcutaneous electrical nerve stimulation in a user, the apparatus comprising:

- a housing;
- an application unit for providing mechanical coupling between said housing and the user's body;
- a stimulation unit mounted to the housing for electrically stimulating at least one nerve with at least one stimulation pulse during a therapy session; and
- a determination unit mounted to the housing and configured to perform at least one of: (i) determining an activity level of the user; (ii) determining a gait characteristic of the user; (iii) determining a balance function of the user; and (iv) determining apparatus placement position on the user.

In another preferred form of the invention, there is provided a method for applying transcutaneous electrical nerve stimulation in a user, the method comprising the steps of:

- securing a stimulation unit and a determination unit to the user's body;
- using the stimulation unit to deliver electrical stimulation to the user to stimulate at least one nerve with at least one stimulation pulse during a therapy session; and
- using the determination unit to perform at least one of: (i) determining an activity level of the user; (ii) determining a gait characteristic of the user; (iii) determining a balance function of the user; and (iv) determining apparatus placement position on the user.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The TENS Device in General

The present invention comprises the provision and use of a novel TENS device which comprises a stimulator designed to be placed on a user's upper calf (or other anatomical location) and a pre-configured electrode array designed to provide electrical stimulation to at least one nerve disposed in the user's upper calf (or other anatomical location). A key feature of the present invention is that the novel TENS device automatically tracks activity, gait, and balance functions and adjusts stimulation parameters according to biomarkers derived from the activity, gait, and balance measures obtained from the user. The novel TENS device also determines the rotational placement position of the device on the leg of a user.

Figure 1:
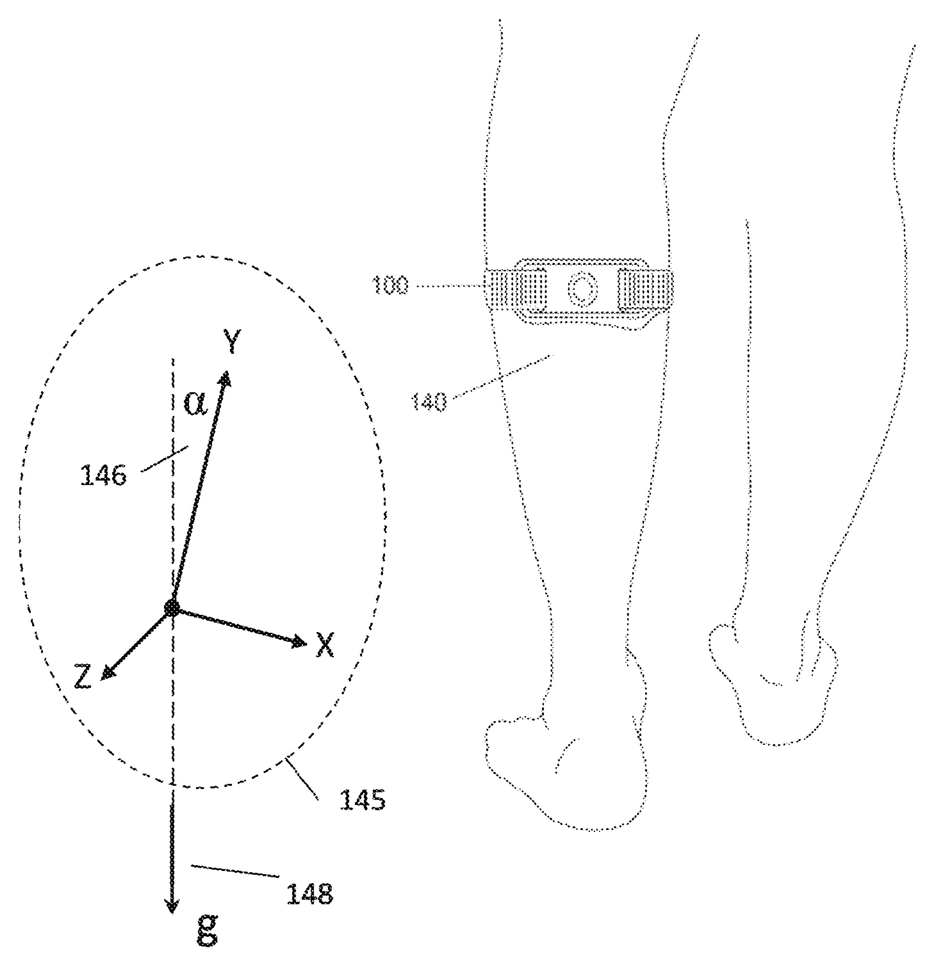
FIG. 1 is a schematic view showing a novel TENS device formed in accordance with the present invention, wherein the novel TENS device is mounted to the upper calf of a user, and also showing the coordinate system of an accelerometer incorporated in the novel TENS device.

More particularly, and looking now at FIG. 1, there is shown a novel TENS device 100 formed in accordance with the present invention, with novel TENS device 100 being shown worn on a user's upper calf 140. A user may wear TENS device 100 on one leg or on both legs (either one at a time or simultaneously), or a user may wear a TENS device 100 on another area of the body separate from, or in addition to, a TENS device 100 worn on one leg (or both legs) of the user.

Figure 2:
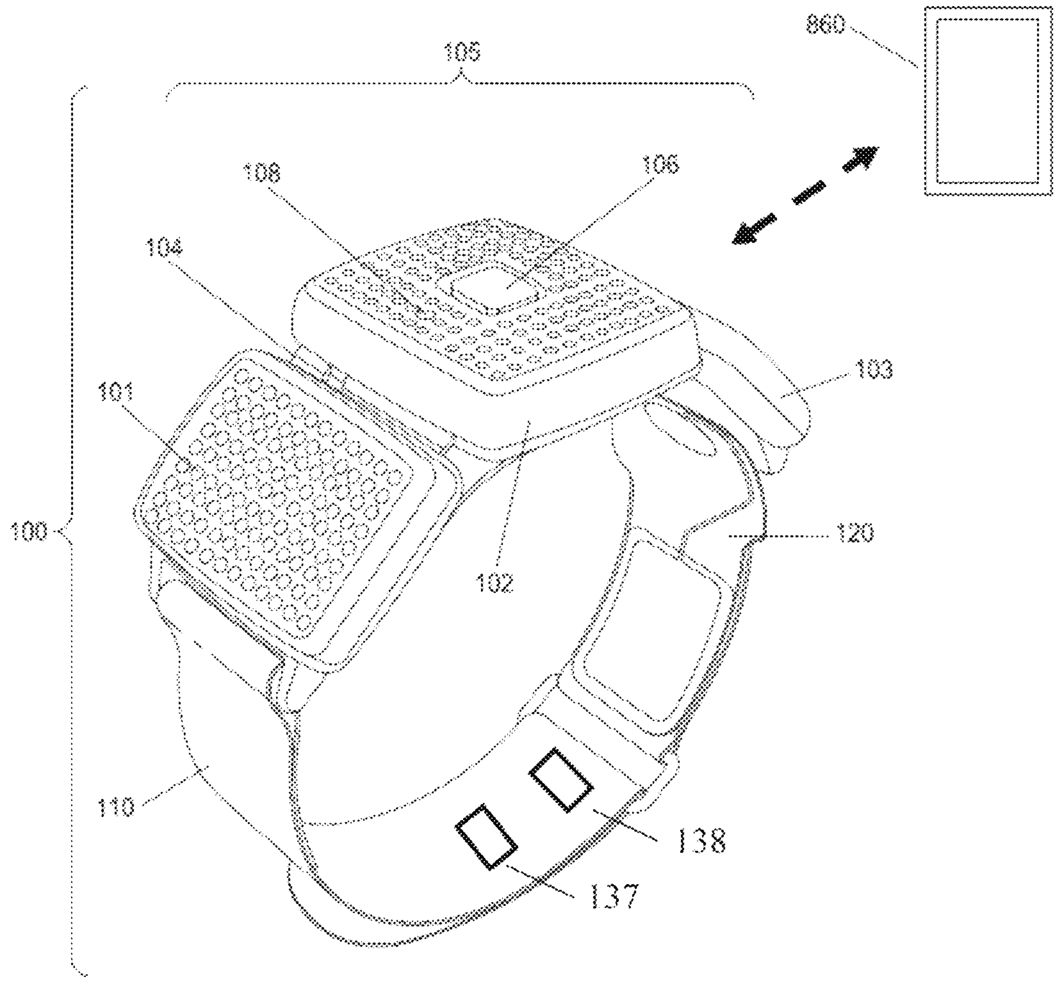
FIG. 2 is a schematic view showing the novel TENS device of FIG. 1 in greater detail.
Figure 4:
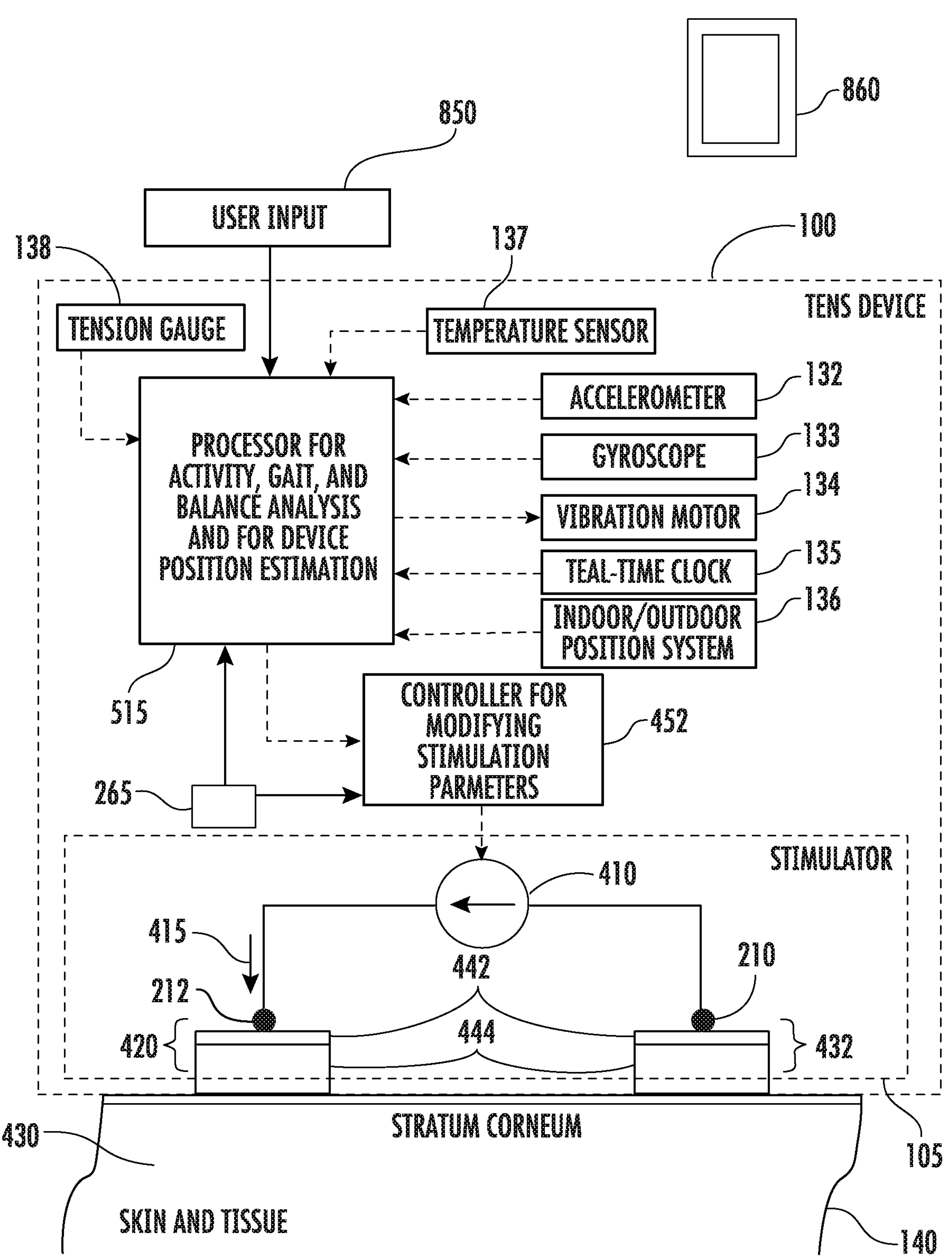
FIG. 4 is a schematic view of the novel TENS device of FIGS. 1-3, including a processor for analyzing activity, gait, and balance, and for analyzing device position.

Looking next at FIG. 2, TENS device 100 is shown in greater detail. TENS device 100 preferably comprises three primary components: a stimulator 105, a strap 110, and an electrode array 120 (comprising a cathode electrode and an anode electrode appropriately connected to stimulator 105). As shown in FIG. 2, stimulator 105 may comprise three mechanically and electrically interconnected compartments 101, 102, and 103. Compartments 101, 102, 103 are preferably interconnected by hinge mechanisms 104 (only one of which is visible in FIG. 2), thereby allowing TENS device 100 to conform to the curved anatomy of a user's leg. In a preferred embodiment of the present invention, compartment 102 houses the TENS stimulation circuitry (except for a battery) and user interface elements 106 and 108. Compartment 102 also houses an accelerometer 132 (see FIG. 4), preferably in the form of a MEMS digital accelerometer microchip (e.g., Freescale MMA8451Q), for detecting (i) user gestures such as taps to central compartment 102, (ii) user leg and body orientation, and (iii) user leg and body motion. Compartment 102 also houses a vibration motor 134 (FIG. 4), a real-time clock 135 (FIG. 4), an indoor/outdoor position system 136 (e.g., a global positioning system of the sort typically referred to as a "GPS"), a temperature sensor 137 (FIGS. 2 and 4), and a strap tension gauge 138 (FIGS. 2 and 4).

In one preferred form of the invention, compartments 101 and 103 are smaller auxiliary compartments that house a battery for powering the TENS stimulation circuitry and other circuitry, and other ancillary elements, such as a wireless interface unit (not shown) of the sort well known in the art for allowing TENS device 100 to wirelessly communicate with other elements (e.g., a hand-held electronic device 860, such as a smartphone, see FIG. 2).

In another form of the invention, only one or two compartments may be used for housing all of the TENS stimulation circuitry, battery, and other ancillary elements of the present invention.

In another form of the invention, a greater number of compartments are used, e.g., to better conform to the body and to improve user comfort.

And in still another form of the invention, a flexible circuit board is used to distribute the TENS stimulation circuitry and other circuitry more evenly around the leg of the user and thereby reduce the thickness of the device.

Still looking at FIG. 2, interface element 106 preferably comprises a push button for user control of electrical stimulation by TENS device 100, and interface element 108 preferably comprises an LED for indicating stimulation status and providing other feedback to the user. Although a single LED is shown, interface element 108 may comprise multiple LEDs with different colors. Additional user interface elements (e.g., an LCD display, audio feedback through a beeper or voice output, haptic devices such as a vibrating element, a smartphone running an appropriate "app", etc.) are also contemplated and are considered to be within the scope of the present invention.

In one preferred form of the invention, TENS device 100 is configured to be worn on the user's upper calf 140 as is shown in FIG. 1, although it should also be appreciated that TENS device 100 may be worn on other anatomical locations, or multiple TENS devices 100 may be worn on various anatomical locations, etc. TENS device 100 (comprising the aforementioned stimulator 105, electrode array 120, and strap 110) is secured to upper calf 140 (or other anatomical location) of the user by placing the apparatus in position against the upper calf (or other anatomical location) and then tightening strap 110. More particularly, in one preferred form of the invention, electrode array 120 is deliberately sized and configured so that it will apply appropriate electrical stimulation to the appropriate anatomy of the user regardless of the specific rotational position of TENS device 100 on the leg (or other anatomical location) of the user.

Figure 3:
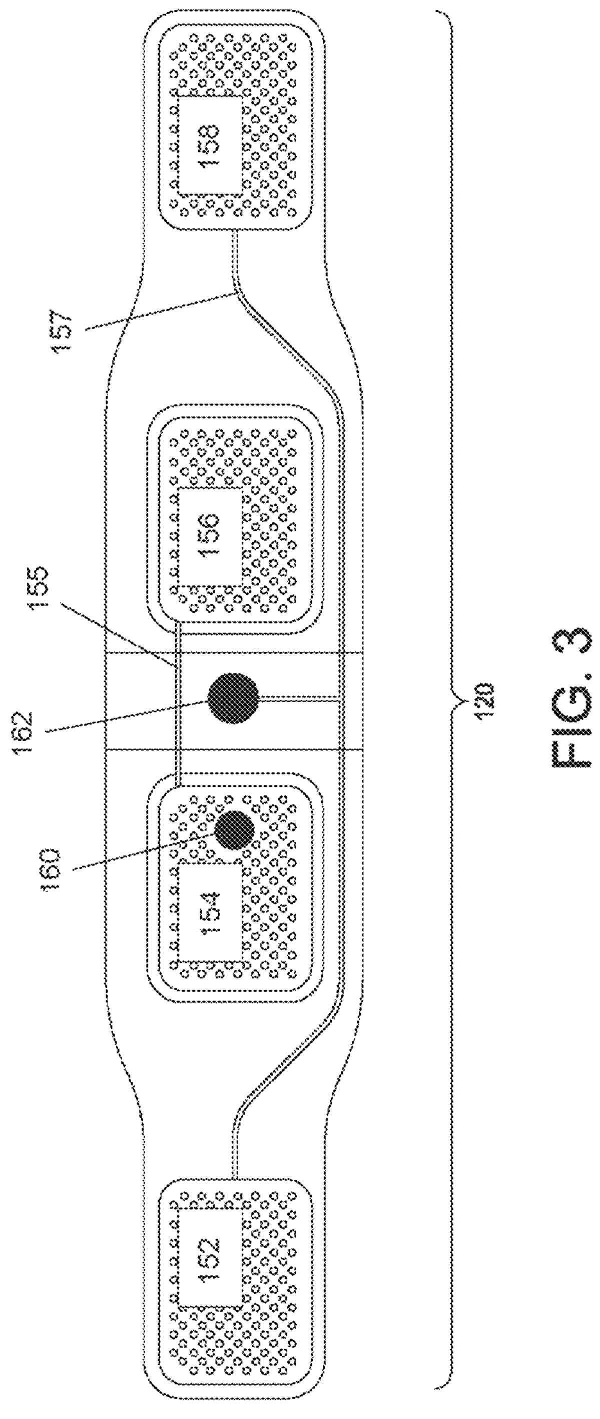
FIG. 3 is a schematic view showing the electrode array of the novel TENS device of FIGS. 1 and 2 in greater detail.

FIG. 3 shows a schematic view of one preferred embodiment of electrode array 120. Electrode array 120 preferably comprises four discrete electrodes 152, 154, 156, 158, each having an equal or similar size (i.e., an equal or similar size surface area). Electrodes 152, 154, 156, 158 are preferably connected in pairs so that electrodes 154 and 156 (representing the cathode of TENS device 100) are electrically connected to one another (e.g., via connector 155), and so that electrodes 152 and 158 (representing the anode of TENS device 100) are electrically connected to one another (e.g., via connector 157). It should be appreciated that electrodes 152, 154, 156, 158 are preferably appropriately sized, and connected in pairs, so as to ensure adequate skin coverage regardless of the rotational position of TENS device 100 (and hence regardless of the rotational position of electrode array 120) on the leg (or other anatomical location) of a user. Furthermore, it should be appreciated that electrodes 152, 154, 156, 158 are not connected in an interleaved fashion, but rather are connected so that the two inside electrodes 154, 156 are connected to one another, and so that the two outside electrodes 152, 158 are connected to one another. This electrode connection pattern ensures that if the two outer electrodes 152, 158 should inadvertently come into contact with one another, an electrical short of the stimulation current flowing directly from cathode to anode will not occur (i.e., the electrode connection pattern ensures that the therapeutic TENS current is always directed through the tissue of the user).

Electrical current (i.e., for therapeutic electrical stimulation to the tissue) is provided to the electrode pairs 154, 156 and 152, 158 by connectors 160, 162 (FIG. 3) which mate with complementary connectors 210, 212 (FIG. 4), respectively, on stimulator 105. Stimulator 105 generates electrical currents that are passed through electrodes 154, 156 and electrodes 152, 158 via connectors 160, 162, respectively.

In one preferred embodiment of the present invention, the skin-contacting conductive material of electrodes 152, 154, 156, 158 is a hydrogel material which is "built into" electrodes 152, 154, 156, 158. The function of the hydrogel material on the electrodes is to serve as an interface between the electrodes 152, 154, 156, 158 and the skin of the user (i.e., within, or adjacent to, or proximal to, the portion of the user's body in which the sensory nerves which are to be stimulated reside). Other types of electrodes such as dry electrodes and non-contact stimulation electrodes have also been contemplated and are considered to be within the scope of the present invention.

FIG. 4 is a schematic representation of the current flow between TENS device 100 and the user. As seen schematically in FIG. 4, stimulation current 415 from a constant current source 410 flows into the user's tissue 430 (e.g., the user's upper calf) via an anode electrode 420 (which anode electrode 420 comprises the aforementioned electrodes 152, 158). Anode electrode 420 comprises a conductive backing (e.g., silver hatch) 442 and hydrogel 444. The current passes through the user's tissue 430 and returns to constant current source 410 through cathode electrode 432 (which cathode electrode 432 comprises the aforementioned electrodes 154, 156). Cathode electrode 432 also comprises a conductive backing 442 and hydrogel 444. Constant current source 410 preferably provides an appropriate biphasic waveform (i.e., biphasic stimulation pulses) of the sort well known in the art of TENS therapy. In this respect it should be appreciated that the designation of "anode" and "cathode" electrodes is purely notational in the context of a biphasic waveform (i.e., when the biphasic stimulation pulse reverses its polarity in its second phase of the biphasic TENS stimulation, current will be flowing into the user's body via "cathode" electrode 432 and out of the user's body via "anode" electrode 420).

Figure 5:
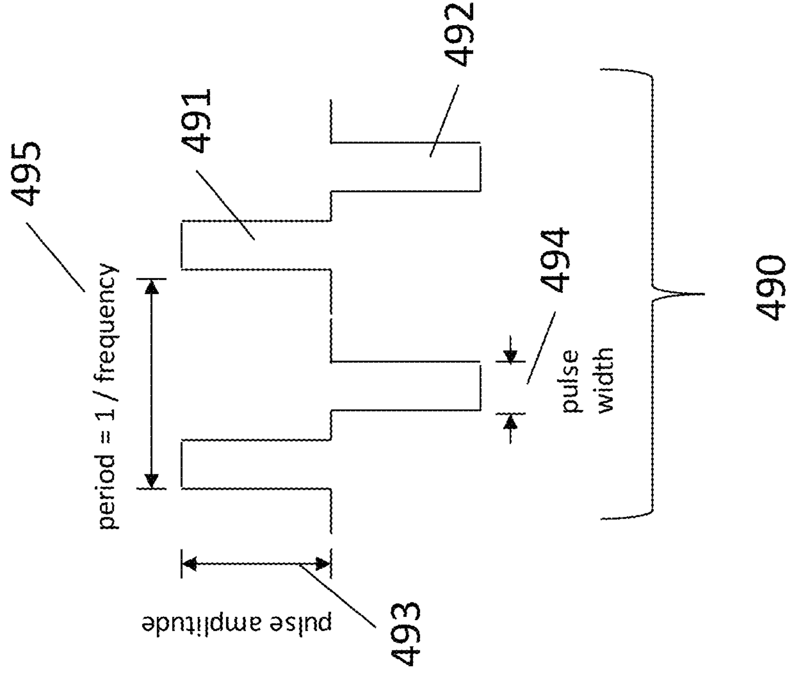
FIG. 5 is a schematic view showing the stimulation pulse train generated by the stimulator of the novel TENS device of FIGS. 1-4.
Figure 5:
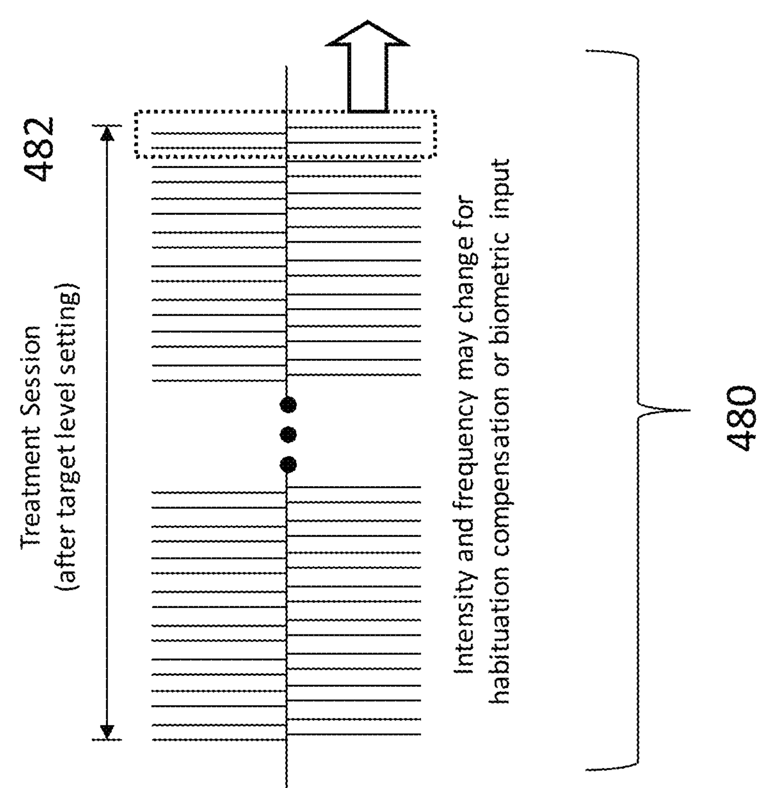

FIG. 5 is a schematic view showing a pulse train 480 provided by stimulator 105 during a TENS therapy session, and the waveform 490 of two individual biphasic pulses, wherein each individual biphasic pulse comprises a first phase 491 and a second phase 492. In one form of the invention, each pulse waveform is charge-balanced across the two phases 491 and 492 of the biphasic pulse, which prevents iontophoretic build-up under the electrodes of the electrode array 120 that can lead to skin irritation and potential skin damage. In another form of the invention, the individual pulses are unbalanced across the two phases of the biphasic pulse, however, charge-balancing is achieved across multiple consecutive biphasic pulses. Pulses of fixed or randomly-varying frequencies are applied throughout the duration of the therapy session 482. The intensity of the stimulation (i.e., the amplitude 493 of the current delivered by stimulator 105) is adjusted in response to user input and for habituation compensation, as will hereinafter be discussed in further detail.

In prior U.S. patent application Ser. No. 13/678,221, filed Nov. 15, 2012 by Neurometrix, Inc. and Shai N. Gozani et al. for APPARATUS AND METHOD FOR RELIEVING PAIN USING TRANSCUTANEOUS ELECTRICAL NERVE STIMULATION (Attorney's Docket No. NEURO-5960), issued as U.S. Pat. No. 8,948,876 on Feb. 3, 2015, and which patent is hereby incorporated herein by reference, apparatus and methods are disclosed for allowing a user to personalize the TENS therapy stimulation intensity according to the electrotactile perception threshold of the user at the time of the setup of the TENS device. The aforementioned U.S. Pat. No. 8,948,876 also discloses apparatus and methods to automatically restart additional therapy sessions after an initial manual start by the user.

In prior U.S. patent application Ser. No. 14/230,648, filed Mar. 31, 2014 by NeuroMetrix, Inc. and Shai Gozani et al. for DETECTING CUTANEOUS ELECTRODE PEELING USING ELECTRODE-SKIN IMPEDANCE, issued as U.S. Pat. No. 9,474,898 on Oct. 25, 2016, and which patent is hereby incorporated herein by reference, apparatus and methods are disclosed which allow for the safe delivery of TENS therapies at night when the user is asleep. These methods and apparatus allow the TENS device to be worn by a user for an extended period of time, including 24 hours a day.

In order to deliver consistently comfortable and effective pain relief to a user throughout both the day and the night, it may not be appropriate to deliver a fixed TENS stimulation level, since the effect of circadian or other time-varying rhythms can mitigate the effectiveness of TENS stimulation. Parameters impacting TENS stimulation effectiveness include, but are not limited to, stimulation pulse amplitude 493 (FIG. 5) and pulse width 494 (FIG. 5), pulse frequency 495 (FIG. 5), and therapy session duration 482 (FIG. 5). By way of example but not limitation, higher amplitude and longer pulses (i.e., larger pulse charges) increase the stimulation delivered to the user (i.e., the stimulation "dose"), whereas shorter therapy sessions decrease the stimulation delivered to the user (i.e., the stimulation "dose"). Clinical studies suggest that pulse charge (i.e., pulse amplitude and pulse width) and therapy session duration have the greatest impact on the therapeutic stimulation delivered to the user (i.e., the therapeutic stimulation "dose").

Assessments of the therapeutic benefits of TENS therapy are often subjective, infrequent, and incomplete, such as those measured by responses to clinical questionnaires or pain diaries. Furthermore, the perception of pain (i.e., the subject's self-evaluation of pain levels) is only one of many important dimensions of effective pain relief. More active lifestyle, steadier gait, and better balance are important examples of improved quality of life and health. These improvements can be attributed to a reduction of pain as a result of TENS therapy. Therefore, one object of the invention is to provide one or more biomarkers that are objectively and automatically measured and are based on assessing the activity, gait, and balance of the user wearing TENS device 100. Another object of the present invention is to permit TENS device 100 to automatically adjust its operations based on the results obtained from monitoring the activity, gait, and balance of the user. A third object of the present invention is to determine the exact placement of TENS device 100 on the upper calf of the user, with placement being determined in terms of the particular limb upon which the TENS device is placed (i.e., left or right leg), and the particular rotational angle $\theta$ (see 402 in FIG. 11) at which the TENS device is positioned.

On-Skin Detector

In one preferred form of the invention, TENS device 100 may comprise an on-skin detector 265 (FIGS. 4 and 12) to confirm that TENS device 100 is firmly seated on the skin of the user.

More particularly, the orientation and motion measures from accelerometer 132 (FIG. 4) and/or gyroscope 133 (FIG. 4) of TENS device 100 only become coupled with the orientation and motion of a user when the TENS device is secured to the user. In a preferred embodiment, an on-skin detector 265 (FIG. 4) may be used to determine whether and when TENS device 100 is securely placed on the user's upper calf.

Figure 6:
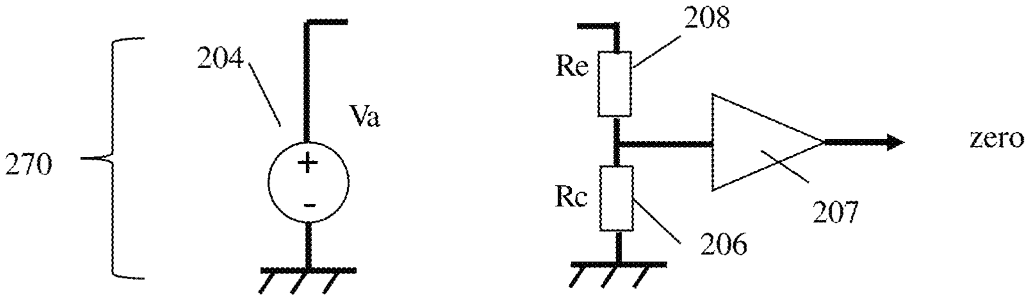
FIG. 6 is a schematic view showing the on-skin detection system of the novel TENS device shown in FIGS. 1-5, as well as its equivalent circuits when the novel TENS device is on and off the skin of a user.
Figure 6:
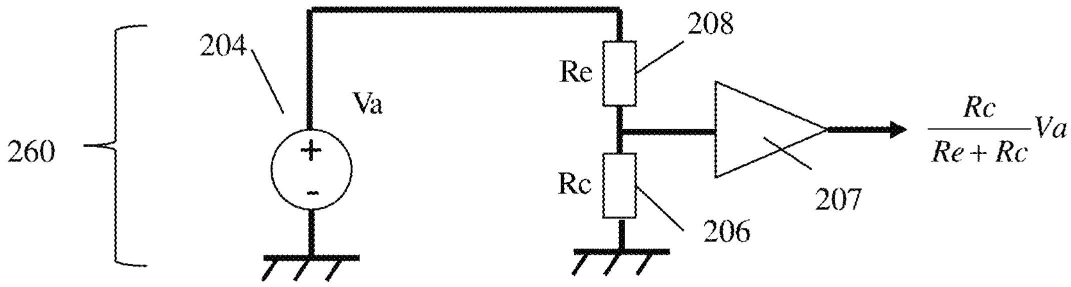
Figure 6:
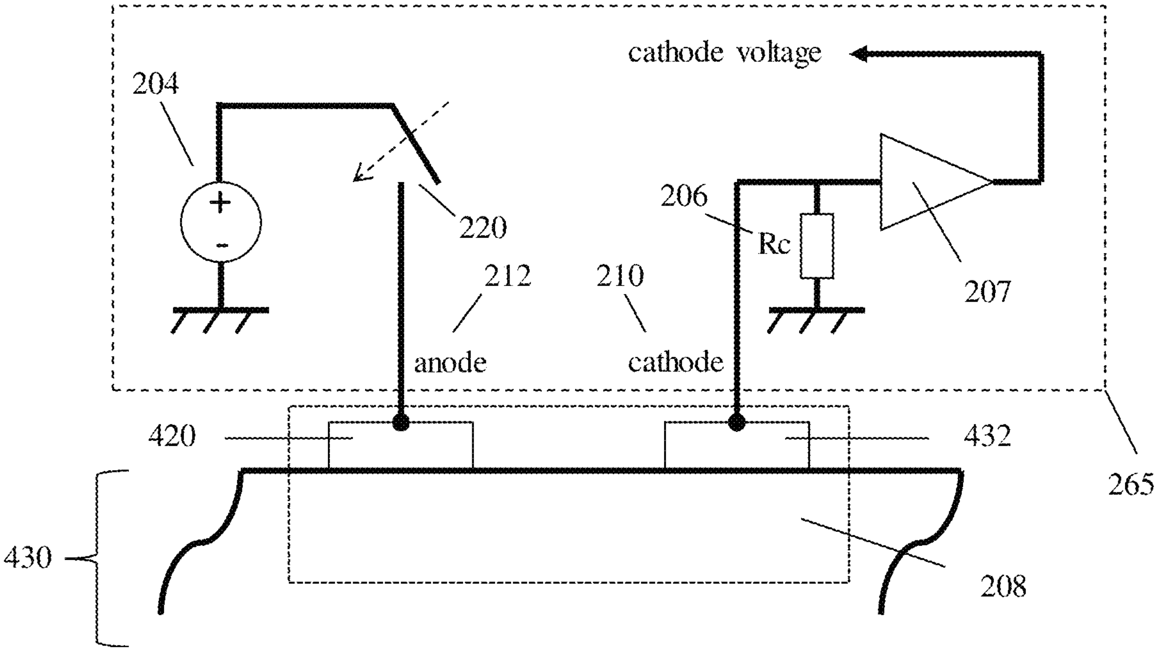

In the preferred embodiment, and looking now at FIG. 6, an on-skin detector 265 may be incorporated in TENS device 100. More particularly, in one preferred form of the invention, a voltage of 20 volts from voltage source 204 is applied to anode terminal 212 of TENS stimulator 105 by closing the switch 220. If the TENS device is worn by the user, then user tissue 430, interposed between anode electrode 420 and cathode electrode 432, will form a closed circuit to apply the voltage to the voltage divider circuit formed by resistors 208 and 206. More particularly, when TENS device 100 is on the skin of the user, the equivalent circuit 260 shown in FIG. 6 represents the real-world system and equivalent circuit 260 allows the anode voltage $V_a$ 204 to be sensed through the voltage divider resistors 206 and 208. The cathode voltage measured from the amplifier 207 will be non-zero and close to the anode voltage 204 when TENS device 100 is secured to the skin of the user. On the other hand, when TENS device 100 is not secured to the skin of the user, the equivalent circuit 270 represents the real-world system and the cathode voltage from amplifier 207 will be zero.

On-skin detector 265 is preferably employed in two ways.

First, if on-skin detector 265 indicates that electrode array 120 of TENS device 100 has become partially or fully detached from the skin of the user, TENS device 100 can stop applying TENS therapy to the user.

Second, if on-skin detector 265 indicates that electrode array 120 of TENS device 100 has become partially or fully detached from the skin of the user, processor 515 (FIG. 4) of TENS device 100 will recognize that the data from accelerometer 132 and/or gyroscope 133 may not reliably reflect user leg orientation and leg motion. In this respect it should be appreciated that when the on-skin detector 265 indicates that TENS device 100 is secured to the skin of the user, such that accelerometer 132 and/or gyroscope 133 is closely coupled to the lower limb of the user, the data from accelerometer 132 and/or gyroscope 133 may be considered to be representative of user leg orientation and user leg motion. However, when the on-skin detector 265 indicates that TENS device 100 is not on the skin of the user, accelerometer 132 and/or gyroscope 133 is not closely coupled to the lower limb of the user, the data from accelerometer 132 and/or gyroscope 133 cannot be considered to be representative of user leg orientation and user leg motion.

An on-skin condition is necessary for the TENS device to stimulate the user inasmuch as a closed electrical circuit is needed for the stimulation current to flow. However, the on-skin condition is not necessary for the TENS device to monitor the user activity, gait, and balance. The TENS device can still perform these monitoring functions and determine placement position of the TENS device as long as the device is positioned on the body.

In one preferred form of the invention, a strap tension gauge 138 (FIGS. 2 and 4) on the TENS device measures the tension of the strap 110. When the strap tension meets a pre-determined threshold, the TENS device 100 is considered "on-body" and the monitoring functions can continue even if the on-skin condition may not be met. In another embodiment, the tension gauge value while the on-skin condition is true is used as the on-body tension threshold. When the on-skin condition becomes false, as long as the tension gauge value is above the on-body tension threshold, the on-body status remains true. All activity, gait, and balance functions can still be performed as long as the on-body status is true. Furthermore, position of the TENS device placement on the body can also be performed as long as the on-body status is true.

In one preferred form of the invention, a temperature sensor 137 (FIGS. 2 and 4) incorporated in the TENS device 100 measures the skin temperature and the skin temperature measurement is used to determine on-body status of the TENS device 100. In a preferred embodiment, the skin temperature measurements during the on-skin condition are averaged and stored as a reference. When the on-skin condition transitions from true to false, the skin temperature is continuously monitored. If the measured skin temperature remains similar to the reference skin temperature, the on-body status is set to true to indicate that the TENS device 100 is still on the user's body. Consequently, all activity, gait, and balance functions can still be monitored. Furthermore, position of the TENS device placement on the body can also be performed as long as the on-body status is true.

Accelerometer Data Sampling

In one preferred form of the invention, TENS device 100 samples accelerometer 132 at a rate of 400 Hz, although a different sampling rate can be utilized.

Device Orientation Determination

In one preferred form of the invention, TENS device 100 (comprising accelerometer 132) is strapped on a user's upper calf 140, e.g., in the manner shown in FIG. 1. The three axes of the accelerometer 132 are shown in FIG. 1 as well. The y-axis of accelerometer 132 is approximately aligned with the anatomical axis of the leg, thus the gravitational force g 148 ("gravity" for short) is approximately parallel to the y-axis of accelerometer 132 when the user is standing. When TENS device 100 is placed on the leg with an "upright" orientation, accelerometer 132 will sense an acceleration value of −g, but when TENS device 100 is placed on the leg with an "upside down" orientation, accelerometer 132 will sense an acceleration value of +g.

In one preferred embodiment, the orientation of TENS device 100 is assessed through device orientation detector 512 (FIG. 12) once on-skin detector 265 determines that TENS device 100 is "on-skin". The y-axis values of accelerometer 132 are accumulated for a period of ten seconds, and then the mean and standard deviation for the y-axis values are calculated. If the standard deviation is below a pre-determined threshold, it suggests that the user has had no activities during that time period (i.e., the ten second time period under review). The mean value is checked against a set of pre-determined threshold values. If the mean value is smaller than −0.5*g, then the device orientation is deemed to be upright. If the mean value is larger than +0.5*g, then the device orientation is deemed to be upside down. If the mean value (i.e., acceleration along the y-axis) is between −0.5 g and +0.5 g, the leg is likely to be in a recumbent position and the device orientation cannot be reliably determined. In this case, a new set of y-axis values will be collected and the above process repeated until the device placement orientation can be reliably determined. Once the device placement orientation is determined, the orientation status of the device stays the same (i.e., upright or upside down) until the on-skin condition becomes "false" (i.e., until the TENS device is determined to no longer be "on-skin") and the device placement orientation returns to an undefined state.

In one preferred form of the invention, the on-skin status will also set the on-body status to true. Temperature sensor 137 and tension gauge 138 can be used to assess the on-body status as disclosed earlier. When the on-skin status becomes "false" due to the loss of electrical contact between the TENS device 100 and the user's skin, the on-body status is assessed based on measurements from temperature sensor 137 or tension gauge 138 or both. The measurement values are compared with a fixed reference threshold or a threshold established during the on-skin period. The device placement orientation status is maintained as long as the on-body status is true.

In one preferred form of the invention, accelerometer measurements acquired from a TENS device placed upside down are mapped to values as if they were collected from a TENS device placed upright in order to simplify data analysis for subsequent activity, gait, and balance assessment. In another embodiment, the data analysis methods are developed separately for data acquired under the two different device orientations (i.e., device upright and device upside down).

In one preferred form of the invention, the activity, gait, and balance assessments (see below) are not performed until the device orientation is determined. In another form of the invention, the activity, gait and balance assessments are performed under the assumption that the device orientation is upright when the device orientation state is undefined. Results obtained under such an assumption are adjusted if the actual device orientation is later determined to be upside down. In yet another form of the invention, the activity, gait and balance assessments are performed under the assumption that the device orientation is the same as the device orientation determined in a previous on-skin session. In yet another form of the invention, the activity, gait and balance assessments are performed under the assumption that the device orientation is the same as the majority of device orientations observed in the past. Regardless of the basis of the assumptions, once the actual device orientation is determined, the activity, gait and balance assessment results are adjusted as needed.

For the sake of clarity, subsequent descriptions will assume that the device placement orientation is upright or that the accelerometer data are mapped to values corresponding to an upright device placement.

Vertical Alignment Compensation

Under the ideal condition (i.e., upright device placement, no external movements such as those experienced on a traveling train, etc.), the y-axis signal from accelerometer 132 stays at the −1*g level (i.e., the static acceleration value caused by earth gravity) when a subject is standing still. The y-axis acceleration value from accelerometer 132 goes above and below this value depending upon leg activities. However, the relative position of the y-axis direction of accelerometer 132 and the direction of earth gravity may not be perfectly aligned (e.g., due to leg anatomy and device placement variations) so the zero activity acceleration value may be different from −1*g.

To determine the exact alignment relationship between the y-axis of accelerometer 132 and earth gravity direction (($\alpha$ 146 in FIG. 1), each time TENS device 100 is placed on the leg of a user (and the "on-skin" condition transitions from false to true), an automated calibration algorithm is preferably used to determine and compensate for any misalignment between the directions of the y-axis of accelerometer 132 and earth gravity. The axes 145 of the accelerometer 132 are shown in FIG. 1. This automated calibration algorithm is shown as device vertical alignment unit 514 in FIG. 12.

In the preferred embodiment, an initial segment of accelerometer data corresponding to the user standing upright (i.e., the y-axis acceleration mean $\gamma_{mean}$ value being greater than a pre-determined threshold) and the user being still (i.e., the y-axis acceleration standard deviation $\gamma_{stdev}$ value smaller than a pre-determined threshold) is analyzed to determine an average of the static gravitational acceleration value. This value is compared with the expected static gravitational acceleration value and the angle ($\alpha$ 146 in FIG. 1) between the two axis directions (i.e., the y-axis acceleration of accelerometer 132 and earth gravity g) can be calculated. The angle $\alpha$ 146 (which essentially identifies misalignment between the y-axis of accelerometer 132 and earth gravity) is then used to compensate for any effects of misalignment of these two axes.

In one preferred form of the invention, the acceleration values from the y-axis of accelerometer 132 are accumulated over a period of ten seconds and the mean is calculated: this value is defined as $\gamma_{mean}$. The angle $\alpha$ 146 (FIG. 1) between the y-axis of accelerometer 132 and the gravity g 148 (FIG. 1) can be estimated with the formula $\alpha=\cos^{-1}/g$).

In another embodiment, multiple estimates of the angle $\alpha$ 146 are averaged and used in subsequent data analysis.

It is often desirable to remove the static gravitational acceleration value from the activity, gait, and balance assessments. Instead of removing −g from the y-axis acceleration measurement, the exact projection of the static gravitation acceleration $-g^* \cos(\alpha)$ is removed to improve the accuracy of the assessments (i.e., the activity, gait and balance assessments). The purpose of this approach is to obtain a better reference to the zero-activity level for the accelerometer data.

Background noise may cause the y-axis acceleration values of accelerometer 132 to fluctuate around the zero-activity level. To compensate for background noise, two times the standard deviation $\gamma_{stdev}$ (see above) is added to, and subtracted from, this zero-activity level in order to create a "zero-activity band". In the preferred embodiment, although the device orientation will only be determined one time for each device "on-skin" session, this zero-activity band is updated whenever a new estimation of $\{\gamma_{mean}, \gamma_{stdev}\}$ becomes available. The upper bound 314 (FIG. 7) of the zero-activity band is referred to as the "positive zero-crossing threshold" and the lower bound 312 (FIG. 7) of the zero-activity band is referred to as the "negative zero-crossing threshold".

Filtering Operation

Figure 12:
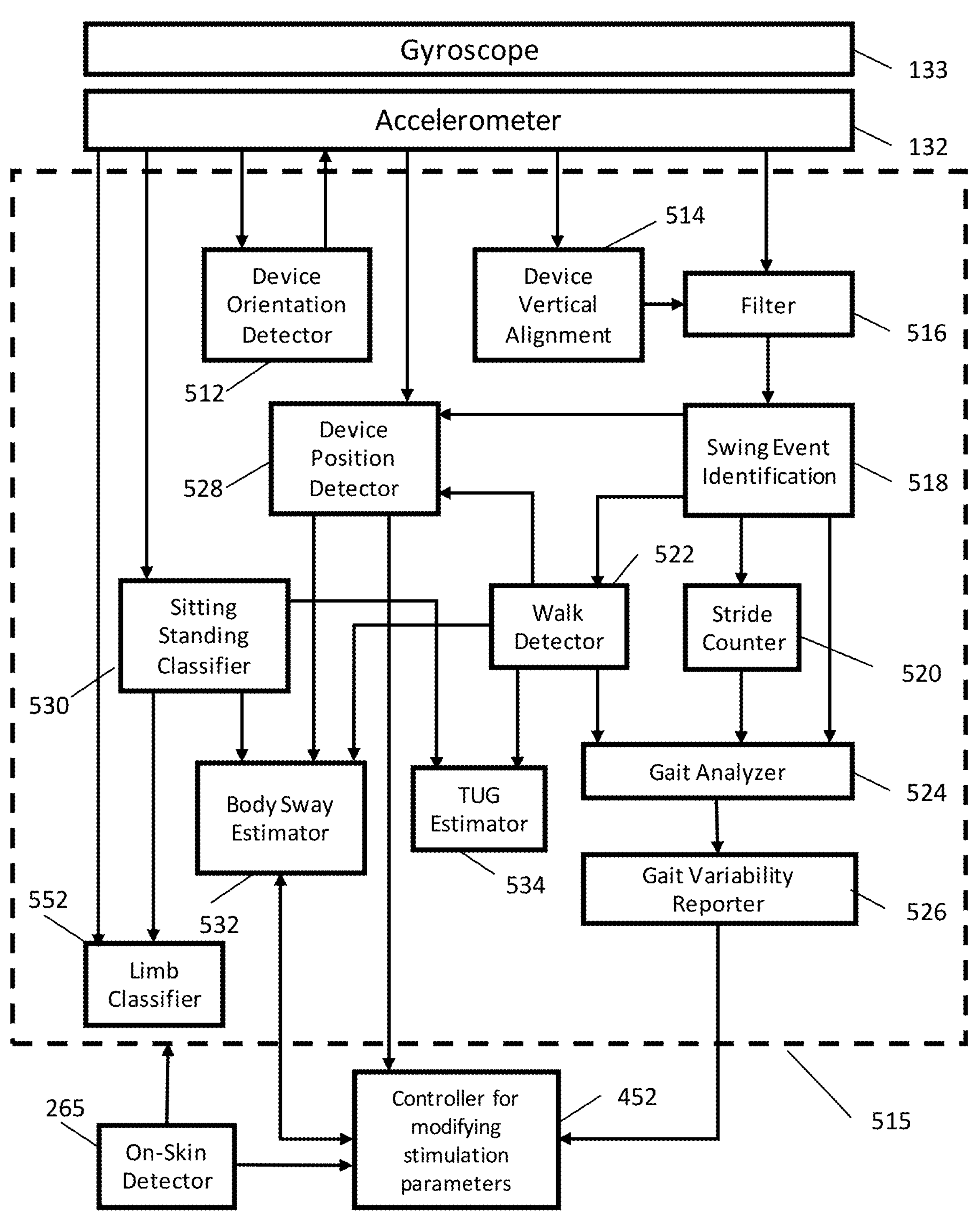
FIG. 12 is a schematic flowchart showing exemplary operation of the novel TENS device, including functionalities for activity monitoring, gait analysis, balance assessment, and device placement position determination.

Filtering operations are designed to preserve waveform features critical to gait analysis while suppressing noise and other inconsequential features. The filter unit 516 (FIG. 12) takes input from accelerometer 132 and setup parameters from device vertical alignment unit 514 to produce output suitable for further processing by swing event identification unit 518 (FIG. 12).

Figure 7:
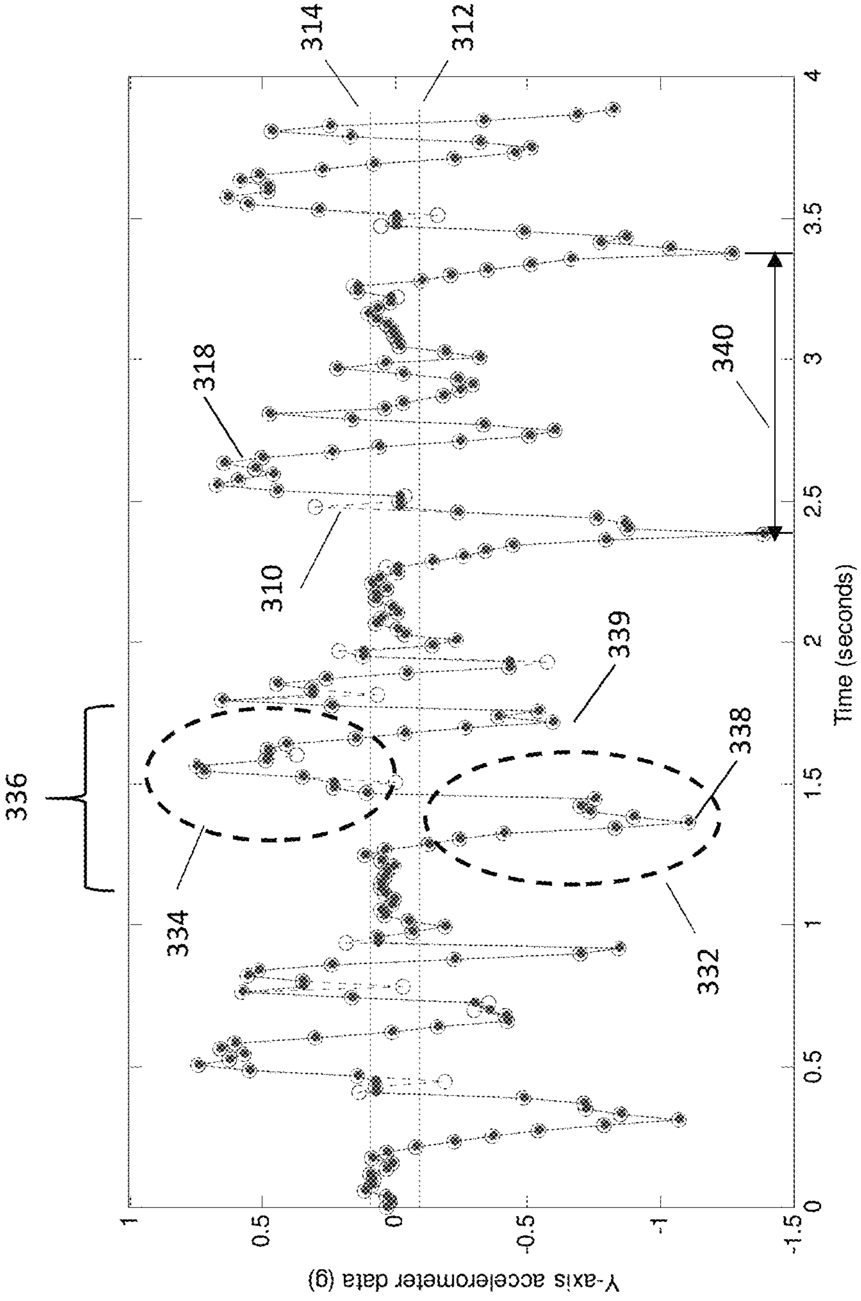
FIG. 7 is schematic view showing an example of the accelerometer data waveform from the y-axis of an accelerometer incorporated in the TENS device, with the accelerometer data waveform showing various characteristic events associated with walking activity.

Looking now at FIG. 7, the open circles connected with dotted lines 310 represent the accelerometer y-axis values after the gravity bias $\gamma_{mean}$ has been removed. The two horizontal lines are the negative zero-crossing threshold 312 and the positive zero-crossing threshold 314. The solid discs connected with solid lines 318 (overlapping lines 310 in many samples) are the filtered accelerometer y-axis values.

Figure 8:
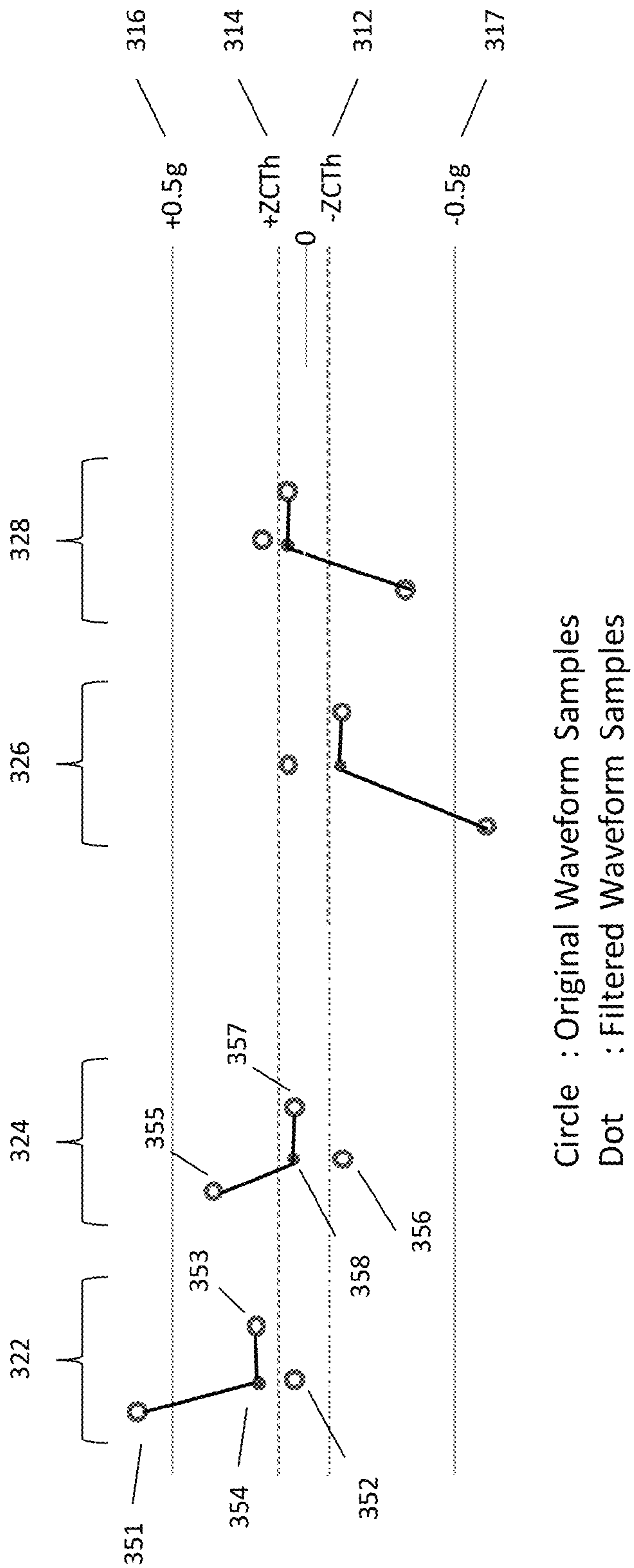
FIG. 8 is a schematic view showing exemplary filter operations performed on the exemplary accelerometer data waveform, and the waveform changes due to the filter operations.

In one preferred embodiment, a selective "median" filter is used to filter the original accelerometer data. The effect of the median filter can be seen in FIG. 7 on waveform samples near or within the zero-activity band (i.e., the region between thresholds 312 and 314) while waveform samples with a larger amplitude are not affected. The median filter is applied selectively to individual waveform samples based on its immediate neighbor sample magnitude. FIG. 8 illustrates the four cases when waveform samples are subject to the median filter operations. The median filter operates on one waveform sample at a time. In case 322, original waveform sample 352 is subject to the median filter operation. The filter examines the two immediate neighboring samples 351 and 353. One of samples 351 has a large amplitude outside the boundary line 316 (e.g., +0.5*g). The filter modifies (i.e., filters) the sample 352 by changing its amplitude to the median of the original amplitude of the three samples 351, 352, and 353. In this case, the median value is that of sample 353. Therefore, the output of the selective median filter for sample 352 will be 354, taking the amplitude value of 353. Median filter operations for case 326 work similarly as that for case 322. In case 324, current waveform sample 356 and its immediate neighbors 355 and 357 are all within a region bounded by boundary line 316 (e.g., +0.5*g) and 317 (e.g., −0.5*g). However, the transition from sample 355 to sample 356 causes waveform to cross the zero activity region (from above to below the region). Additionally, the amplitude difference between the current sample 356 and either neighbor sample exceeds a threshold 0.75*g. Under these conditions, the filter modifies the amplitude of the current sample 356 to the median of the original amplitudes of the three samples 355, 356, 357. In this case, the median value is that of sample 357. Therefore, the output of the selective median filter for sample 356 will be 358. Median filter operations for case 328 work similarly as that for case 324. Median filter operations for case 328 work similarly as that for case 324. In other cases, the current sample retains its original amplitude value. It is noted that a threshold crossing event could still occur even after application of the median filter depending upon the exact value of the neighboring sample points. It is also noted that the values of +0.5*g (which is used to set boundary line 316), −0.5*g (which is used to set boundary line 317), and 0.75*g (which is used to help determine applicability of median filter operations on the current sample) are those chosen for one preferred form of the invention, other values may be used and are considered to be within the scope of the present invention.

Swing Event Identification

Swing event identification unit 518 (FIG. 12) identifies leg swing events based on specific characteristics of accelerometer waveforms. The following characteristics are evident for the filtered y-axis accelerometer data waveform 318 (FIG. 7) associated with a leg swing event 336 (i.e., a stride) (FIG. 7) when the user is making a stride: a segment (negative phase, 332 in FIG. 7) of the waveform is below the negative zero-crossing threshold 312, followed immediately by a larger segment (positive phase, 334 in FIG. 7) of the waveform being above the positive zero-crossing threshold 314. Areas of the positive and negative phases are calculated. For the purpose of area calculation, the magnitude of each sample is limited to 1*g to minimize the effect of large acceleration spikes. The area of the smallest rectangle that covers the magnitude-limited positive phase (i.e., "the positive rectangular area") is also calculated. A stride (e.g., leg swing event 336 in FIG. 7) is recognized if all of the following conditions are met:

1. the positive phase duration is no greater than a first threshold Th1;
2. the positive phase duration is no shorter than a second threshold Th2;
3. the swing event is not too close to a previously-detected swing event (i.e., the difference in the timings of the two events is greater than a pre-determined threshold);
4. the area of the positive phase (334 in FIG. 7) is no smaller than a third threshold Th3;
5. the "positive rectangular area" is no smaller than a fourth threshold Th4, or the combined area of the positive and negative phases (332 and 334 in FIG. 7) is no smaller than 1.5 times the threshold Th4; and
6. the maximum amplitude of the positive phase (334 in FIG. 7) is no smaller than a fifth threshold Th5, or the peak-to-peak amplitude (i.e., the positive phase peak waveform value minus the negative phase peak waveform value) is no smaller than a sixth threshold Th6.

Each leg swing event 336 (FIG. 7) which is identified adds one stride to a stride count (which is recorded in a counter or register) through a stride counter 520 (FIG. 12). The step count is defined as twice the stride count for any measurement period. The timing for each stride is anchored to a "toe-off" event, which is the time instance 338 (FIG. 7) associated the valley of the waveform 318. The "toe-off" event corresponds to the time instance when one foot is moving off the ground immediately prior to the swinging of the leg forward. The time difference between two consecutive toe-off events (340 in FIG. 7) is called the stride duration if the time difference is below a threshold (e.g., 3 seconds). Cadence is calculated by dividing the step count by the time interval corresponding to the steps taken.

In another embodiment, gyroscope data (from gyroscope 133, FIG. 4) are used to detect and quantify leg swing activities. Gyroscope 133, incorporated in TENS device 100 (which is attached to the leg of the user), can measure the angular acceleration and velocity of the leg during leg swing periods.

WalkNow Status Indicator

In one preferred form of the invention, TENS device 100 also comprises a walk detector 522 (FIG. 12) to set the "WalkNow status indicator". The WalkNow status indicator is set to FALSE by default. When five or more strides are detected, the average stride duration is calculated if no two consecutive strides are separated by more than a pre-determined threshold time interval (e.g., 5 seconds). If the average stride duration is no greater than the pre-determined threshold time interval, then the WalkNow status indicator is set to TRUE. If at any time two consecutive strides are separate by more than the threshold time interval, then the WalkNow status indicator is reset to FALSE. The cumulative time intervals during which the WalkNow status is set to TRUE form the Walk Duration value (which is also stored in a counter or register).

Gait Analysis

The primary objective of gait analysis is to assess and characterize gait variability. Gait variability is an effective predictor of fall risk (Hausdorff et al, Gait variability and fall risk in community-living older adults: a 1-year prospective study. Arch Phys Med Rehabil., 2001;82(8):1050-6). In one preferred form of the invention, stride duration variability is measured. Stride durations are obtained when the TENS user is in his or her natural walking environment. This is in contrast to most gait variability measurements that are done in a laboratory setting. A coefficient of variation (CoV) value is calculated for each qualified walk segment. A walk segment is a sequence of consecutive strides when the WalkNow status remains true. A qualified walk segment is a walk segment whose stride characteristics meet certain criteria, such as the number of strides exceed a minimum threshold. Because the walking environment may influence gait variability, the daily distribution of CoV (percentile values) is updated and reported to the user whenever a qualified walk segment becomes available. The major functional blocks of gait analyzer unit 524 (FIG. 12) include:

1. toe-off event detection;
2. gait segment determination; and
3. gait variability estimation.

Figure 9:
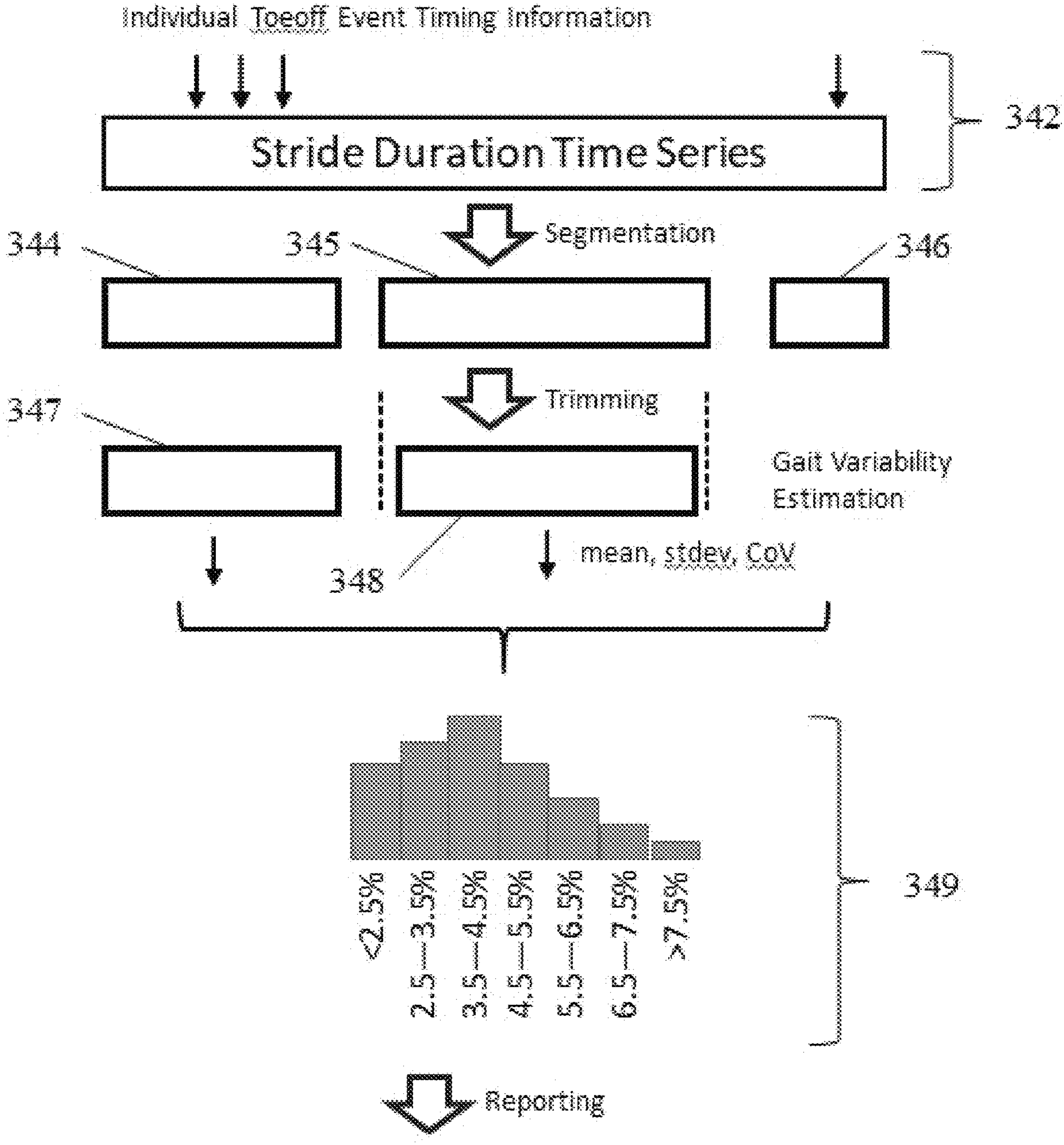
FIG. 9 is a schematic view showing processing steps for determining gait variability metrics based on a stride duration time series.

A flowchart summarizing gait analysis is shown in FIG. 9.

Toe-Off Event Timing Detection

Walking involves periodic movements of legs. Any readily identifiable event of leg movement can be used to mark the period of the periodic movements (stride duration). Two events, the "heel strike" and toe-off events, are commonly used for stride duration estimation and gait variability analysis. The "heel strike" event is the time instance when the heel of a foot makes the initial contact with the ground during walk. The "toe-off" event corresponds to the time instance when a foot is moving off the ground immediately prior to the swinging of the leg forward. In one preferred embodiment, toe-off events are used in gait analysis. Exact toe-off event timing is traditionally obtained through examining force-mat or force sensor measurements. However, measurements from accelerometer 132 incorporated in the TENS device (which is attached to upper calf of the user) provide distinct features that are highly correlated with actual toe-off events. In one preferred form of the invention, the timing of negative peaks 338 (FIG. 7) prior to the positive phase 334 (FIG. 7) are used to approximate the timing of the toe-off events. Although the timing of negative peaks 338 may not coincide precisely with the actual toe-off time, the relationship between the two is strong and provide a high correlation. Stride durations derived from a force-sensor (for actual toe-off events) and those derived from accelerometer 132 using negative peaks 338 also exhibit very high correlation under various gait conditions (e.g., walk at normal pace, walk at faster pace, walk at slower pace, etc.).

Once a stride (336, a positive phase 334 following a negative phase 332) is detected, recorded negative peaks 338 are examined within a time window prior to the stride detection event. In one preferred embodiment, the negative peak 338 with the largest amplitude is identified and its timing is used as the toe-off event time. If no negative peak 338 exists within the search window, then the timing of the negative peak 338 that is closest to stride detection event is used.

In yet another embodiment, similar features of the accelerometer signal from an axis other than the y-axis are used to determine toe-off events. The difference between two consecutive toe-off events is recorded as a stride duration.

Stride Duration Series Segmentation

Stride duration time series 342 (FIG. 9) is accumulated for the duration of each walk segment. If the number of stride duration measurements exceeds a maximum count, the stride duration series is divided into a plurality of segments (each up to the maximum count). In one preferred embodiment, the mean and standard deviation for each segment of the stride duration series are calculated and an outlier threshold is set based on calculated mean and standard deviation values. Stride durations are flagged as outliers if the absolute values of the differences from the mean exceed the outlier threshold. These outliers, if any, divide the original series into smaller segments of consecutive stride durations for gait variability assessment. FIG. 9 shows three such segments 344, 345, and 346 derived from a stride duration time series 342.

Stride Duration Segment Trimming

Still looking at FIG. 9, for each segment having a segment length (segment length is the number of stride durations in the segment) exceeding a minimum segment length (e.g., 30 strides), the segment becomes an eligible gait variability assessment segment 345. Statistics of the duration time series are calculated for each eligible gait segment. Before calculation, the first and last five stride duration samples of the segment are temporally trimmed to form a middle segment. The maximum absolute difference of the samples from the middle segment mean is calculated. The middle segment is then expanded, sample by sample, to include contiguous adjacent samples from the first five until the sample difference from the mean exceeds the maximum absolute difference. The expansion to include durations from the last five samples proceeds similarly. As a result of this operation, each segment 347 (FIG. 9) and 348 (FIG. 9) contains a series of stride durations suitable for gait variability estimation.

Gait Variability Estimation

For each eligible segment 347 and 348, the mean and standard deviation values of the stride duration samples are calculated. The coefficient of variation (CoV) is also calculated. In one preferred embodiment, the daily minimum CoV is maintained for each user as the gait variability metric. In another embodiment, the gait variability metric is a histogram 349 (FIG. 9) of the CoV (in percentage values) with the following bins: <2.5%, 2.5%-3.5%, 3.5%-4.5%, 4.5%-5.5%, 5.5%-6.5%, 6.5%-7.5%, and >7.5%. The gait variability metrics are reported through a gait variability reporter unit 526 (FIG. 12) to the user whenever an eligible gait analysis segment becomes available. In another embodiment, gait variability metrics is reported under different step cadence conditions. For example, gait variability of slow leisure walking is reported separately from the gait variability of brisk walking.

Balance Monitoring

The ability to maintain balance is an important health indicator. Balance can be assessed under various conditions. Both population-based comparisons and subject-based comparisons can be performed. In one preferred embodiment, the three-axis accelerometer 132 is used to measure leg movement with its y-axis parallel to the anatomical axis of the leg. Leg motions caused by body sway in the transverse planes are sensed by the x- and z-axis components of accelerometer 132. The accelerometer data from x- and z-axis are used to quantify the balance of the subject through a body sway estimator unit 532 (FIG. 12).

Figure 10:
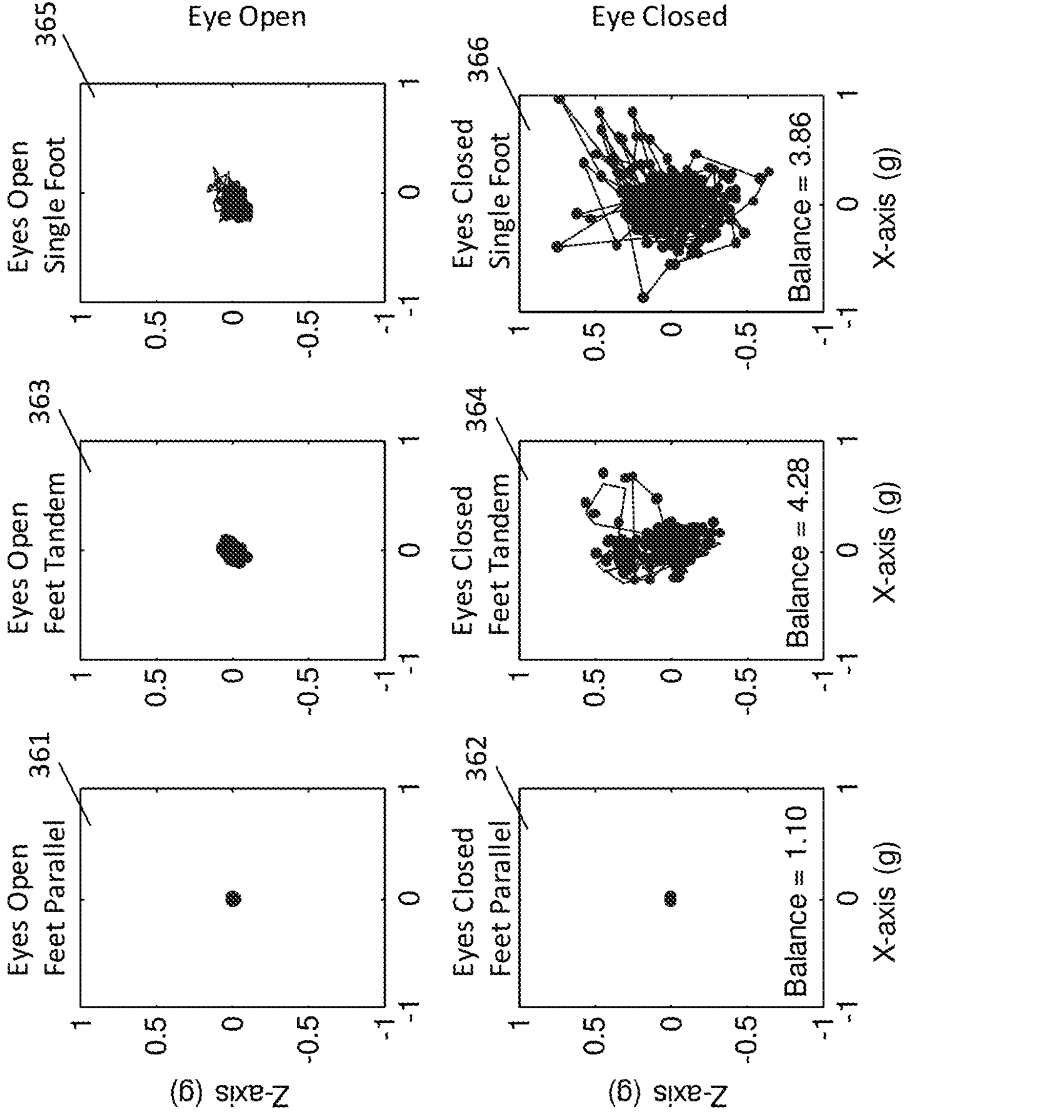
FIG. 10 is a schematic view showing accelerometer measurements in the x- and z-axis directions for assessing the balance of a user under exemplary test conditions.

In one preferred form of the invention, when a subject is standing still on a flat and solid surface with their eyes open, x/z-axis sample pairs are traced as a function of time, e.g., as shown in plot 361 of FIG. 10. In one preferred embodiment, the standing duration is set at 10 seconds. Body sway (i.e., trajectories of the x- and z-axis accelerometer data) is quantified by the standard deviation along the x-axis and the z-axis. In another preferred embodiment, a linear combination of the two directional standard deviations (i.e., the standard deviations of the x- and z-axis data) is used to quantify the data variability. This variability serves as the baseline reference internal to the TENS user. Then the user attempts the same balance test, but with their eyes closed (plot 362 in FIG. 10). The variability in the accelerometer data is calculated in a similar manner and the ratio between the variability measures under the "eye closed" case and the "eye open" case serves as a balance metric for the user. The "eye open" and "eye closed" conditions can be tagged with user input 850 (FIG. 4) or via smart device 860 (FIG. 4) which is connected to the TENS device 100 (e.g., via Bluetooth).

In another embodiment, the two feet of the user are positioned in tandem. Variability measurements under "eye open" and "eye closed" conditions can be compared with each other to determine the balance ability of the user (plots 363 and 364 of FIG. 10). Additionally, variability measurements from the "feet in tandem" condition and the "feet in parallel" condition can also be compared to quantify the balance of the user.

In yet another embodiment, only a single foot of the user (i.e., the foot at the end of the leg carrying the TENS device) is on the ground and variability measures under "eyes open" and "eyes closed" conditions are compared with each other and are compared with both feet on the ground in parallel condition (plots 365 and 366 in FIG. 10).

In another embodiment, the sway path length (i.e., the summation of the sample-to-sample distances in the aforementioned two-dimensional plots) is used as the variability measure. The sample-to-sample distances are the Euclidian distance, or any other distance measures, which quantify the spatial distance between two points. In yet another embodiment, the maximal sway amplitude (i.e., the largest distance between any two samples within a given time interval) is used as the measure of balance variability. In yet another embodiment, the frequency of body sway is calculated for use as a measure of balance variability. In yet another embodiment, the variability of body sway frequency is used as a measure of user balance.

In another embodiment, an electrical stimulation is given to the user as a disturbance after a baseline variability measure without electrical stimulation has been obtained.

The "worst" (i.e., largest) variability within a given time period immediately following the electrical stimulation is estimated, and the ratio between the two variability measures is used as a balance metric for the user. In another embodiment, the time it takes for the body sway variability to return to a baseline value prior to a disturbance is used as a balance metric.

In another embodiment, the disturbance is a mechanical stimulation such as a vibration from a vibration motor 134 (FIG. 4) incorporated in TENS device 100.

In another embodiment, the "getting up and go" events of the user (i.e., the transition from a sitting position to taking a step) are monitored using the accelerometer data from accelerometer 132. The time interval that the user takes to complete the "getting up and go" event is tracked as another balance metric.

In yet another embodiment, the number of strides needed to achieve a steady gait (using the user's own gait stability metrics as a reference) is measured as a balance metric.

Significantly, with the present invention, balance metrics can be obtained and tracked during normal use of the TENS device. Typically, the TENS device (e.g., Quell®, Neurometrix, Inc., Waltham, Ma., USA) is worn by its user at least several hours a day while the user engages in routine daily activities. In one preferred embodiment, accelerometer data from accelerometer 132 are monitored continuously and sections of the data corresponding to "standing still" are identified, segmented, and analyzed. Body sway parameters based on these segments are estimated and a histogram of parameter values is constructed to determine daily balance metrics. In another embodiment, transitions from sitting to walking are tracked, and transition time intervals are recorded, in order to construct a daily profile for assessing balance functions.

In another embodiment, the user can tag his or her conditions (e.g., "about to stand up from a sitting position", "walking on an uneven surface", etc.) manually via a connected device 860 (FIG. 4) such as a Bluetooth-enabled smartphone or through direct gesture to the TENS device (user input 850 in FIG. 4) so that specific activity, gait, and/or balance metrics can be interpreted accordingly. In yet another embodiment, contextual tags can also be applied automatically to the activity, gait and/or balance metrics, e.g., the time of the day, the time since waking up (when sleep monitoring functionality is incorporated into the TENS device), the time before or after a certain amount of activities (e.g., after walking 5000 steps), the user location (e.g., via the indoor/outdoor position system 136 in FIG. 4, which may be a GPS), etc. With the contextual information, gait variability patterns over a period of days can be constructed to determine the gait variability trend. For example, gait variability during the early morning walk along the same walk path can be tracked and compared to determine whether an improvement in gait variability is evident when the TENS user utilizes the TENS therapy daily.

Rotational Position Determination

Another aspect of the present invention is to automatically determine the rotational position of TENS device 100 on the leg of a user through device position detector unit 528 (FIG. 12). Once TENS device 100 is placed on the leg of a user, it stays in position until it is removed from the body. The placement and removal events can be detected via on-skin detector 265 in the manner previously disclosed.

Figure 11:
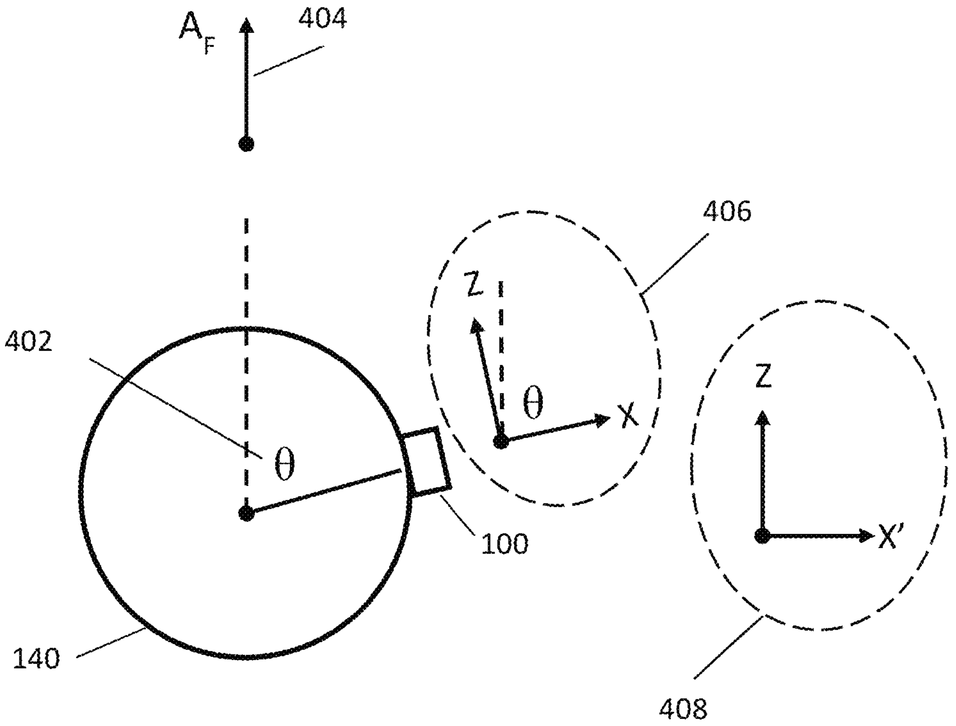
FIG. 11 is a schematic view showing an exemplary coordinate system transformation and its utility to determine the rotational position of the novel TENS device based on forward motion acceleration during a walking period.

FIG. 11 shows a cross-section (transverse plane) of leg 140 and an exemplary rotational position of TENS device 100 on the leg. The rotational position of TENS device 100 is defined by the angle 402 (denoted as θ in FIG. 11) between TENS device 100 and the "forward motion" direction 404 (FIG. 11). It should be noted that the aforementioned stride detection algorithm based on the y-axis accelerometer data from accelerometer 132 functions fully without requiring knowledge of the rotational angle θ.

During the positive phase 334 (FIG. 7) identified by the aforementioned stride detection algorithm, the acceleration associated with forward leg movement (i.e., when the y-axis acceleration value is above the positive zero-crossing threshold 314) is projected onto the x- and z-axis coordinate system 406 (FIG. 11) of accelerometer 132. By way of example but not limitation, if the angle is θ 402 is 90 degrees (i.e., TENS device 100 is placed on the right side of a limb), the forward acceleration $A_F$ 404 will have zero projection on the x-axis ($A_F$*cos θ=0) and maximum projection on the z-axis ($A_F$*sin θ=$A_F$). By way of further example but not limitation, if TENS device 100 is placed at the posterior position (i.e., on the back of the leg) with an angle θ=180, the forward acceleration $A_F$ 404 will have a negative projection on the x-axis ($A_F$*cos θ=−$A_F$) and a zero projection on z-axis ($A_F$ * sin θ=0).

In one preferred embodiment, the x- and z-axis acceleration measurements are acquired during the positive phase 334 (FIG. 7) of leg swing motions. The averages of the x- and z-axis acceleration data over 20 consecutive strides are obtained: these are defined as $\overline{A}_x$ and $\overline{A}_z$. The rotational angle θ 402 is estimated via a $\overline{\theta}=\tan^{-1}(\overline{A}_z/\overline{A}_x)$. Because the periodicity of the tangent function is 180 degrees, the ambiguity of an estimated angle $\overline{\theta}$ belonging to the 0-90 degree range, or belonging to the 180-270 degree range, is resolved based on the signs of $\overline{A}_x$ and $\overline{A}_z$. When the signs of $\overline{A}_x$ and $\overline{A}_z$ are both positive, $\overline{\theta}$ belongs in the 0-90 degree range; otherwise $\overline{\theta}$ belongs in the 180-270 degree range.

In one preferred embodiment, an individual estimate of angle $\overline{\theta}$, once it becomes available, is used as the current rotational position of TENS device 100. In another embodiment, the rotational position is a cumulative average of all available individual estimates of the angle obtained since the on-skin event starts. In yet another embodiment, the rotational position of TENS device 100 is a weighted average of the individual angle estimates obtained since the on-skin event starts. In this form of the invention, the angle estimates obtained more recently are given a higher weight factor in the weighted average.

With the knowledge of the rotational position of TENS device 100, the measured accelerations in the coordinate system 406 (FIG. 11) of the x- and z-axis of accelerometer 132 can be mapped to the coordinate system 408 (FIG. 11) of the leg with an x'-axis considered to be in the medial-lateral direction (i.e., the coronal plane) and the z'-axis considered to be in the anterior-posterior direction (i.e., the sagittal plane) through the well-known "rotation of axes" translation:

$$A_{x'}=A_x \sin\theta-A_z \cos\theta \text{ and } A_{z'}=A_x \cos\theta+A_z \sin\theta.$$

The mapped values $A_{x'}$, and $A_{z'}$ in the x'-z' axes coordinate system, provide a direct measure of lateral-medial sway ($A_{x'}$) and anterior-posterior sway ($A_{z'}$) of the leg and the body. The magnitude and frequency of direction-specific sways allow TENS device 100 to further determine the state of the leg wearing TENS device 100 for balance assessment.

Under the general condition of zero activity of the y-axis accelerometer data, defined as the acceleration values $A_y$ (after the static gravitational value $\gamma_{mean}$ is removed) within the zero-activity band bounded by positive and negative zero-crossing thresholds 312 and 314 (FIG. 7), it can be assumed that the user is either standing or sitting (with feet on the ground). Sitting standing classifier unit 530 (FIG. 12) is designed to differentiate between sitting and standing states of the TENS device user.

When sitting, the legs of a user tend to be either quiet or in short periods of smooth motions in lateral-medial directions. Such smooth motions of legs with feet anchored on the floor will result in acceleration along the x'-axis direction (positive or negative). Additionally, either leg could be positioned, in a steady state, at an angle not perpendicular to the ground (e.g., leaning laterally). To determine such a case, the acceleration data in y-axis direction are analyzed in overlapping time windows. If the standard deviation is small (i.e., steady) and mean is smaller than the estimated $\gamma_{mean}$ in absolute value, then the user is likely to be in a sitting position during the time window.

A different set of feature characteristics can be expected when the user is standing. More particularly, a short period of minimum activities in the y-axis direction, sandwiched between two walking segments, is likely to be a standing period. Periodic and small forward-backward motions in the z'-axis direction is also indicative of standing. If periodic motion is present in both the x'- and z'-axis directions, the x'-axis direction motion is expected to be smaller than the z'-axis direction motion as people tend to stabilize themselves with two feet apart (in the lateral-medial x'-axis direction).

In one preferred form of the invention, TENS device 100 continuously monitors and processes, in the background, accelerometer data in the y-axis direction to differentiate between periods of high activity and low activity. High activity periods typically correspond to walking, running, or other activities involving feet on/off the ground (thus a high activity in the direction parallel to gravity). Low activity periods typically correspond to standing and sitting where the y-axis accelerometer data maintain a mean value close to gravity but with small variations. To discriminate between standing and sitting, relative activities in the x'- and z'-axis directions (the coordinate system invariant to TENS device rotational placement) are examined. Large amplitude and low frequency acceleration elements in x'-axis direction, when compared to that of z'-axis direction data, are indicative of sitting, with most likely leg movement of swaying laterally with feet anchored on the floor. High frequency and small amplitude elements are indicative of body sways while standing, particularly if activities in the coronal plane (the medial-lateral direction) are lower than those in the sagittal plane (the anterior-posterior direction).

With the identification of standing and sitting states, the apparatus disclosed in this application can measure balance metrics automatically without user interventions. In one preferred embodiment, when standing is detected, body sway metrics such as standard deviation of 10-second acceleration data in the x'- and z'-axis directions are calculated. In one preferred embodiment, the standard deviations are averaged to obtain a daily average to determine the standing balance metric. In another preferred embodiment, a linear combination of the two directional standard deviations is used to quantify the data variability as a biomarker for balance.

When sitting is detected, TENS device 100 enters into a mode to measure the "timed up and go" (TUG) time through a TUG estimator unit 534 (FIG. 12). In one preferred embodiment, the time difference between the first stride and the first sudden movement immediately prior to the first stride is tracked automatically. During the sitting state, a sudden spike in acceleration measurement in the x'- and z'-axis directions is indicative a sudden leg movement. Timing of the detected spike events is stored in a circular buffer. When the first stride during a walk segment is detected, the timing of the last detected spike event marks the start of the TUG event. Timing of the first detected stride marks the end of the TUG event. In one preferred embodiment, the stride detection time is the time of the toe-off event (338 in FIG. 7) associated with the stride. Timing of other identifiable events associated with a stride can also be used, such as the heel strike time (local minimum after the swing phase, 339 in FIG. 7). In one preferred embodiment, the median of daily TUG time is used as a biomarker to quantify balance functions of the user. In another embodiment, the minimum of daily TUG time is used as the biomarker to quantify the balance functions of the user. In yet another embodiment, a histogram of daily TUG time is used as the biomarker for the balance function of the user.

Limb Classifier

The determination of the rotational position of the TENS device 100, as disclosed above, works equally well regardless of on which leg the device is placed. However, limb determination can also be achieved with the present invention through a limb classifier unit 552 (FIG. 12). More particularly, and looking now at FIG. 11, the position of TENS device 100 can be on the lateral side of the right leg or the medial side of the left leg. In one preferred embodiment, gravity projection on the x'-axis is constantly monitored during a sitting period to resolve ambiguity of which limb has the TENS device thereon (i.e., left leg versus right leg). While sitting and relaxed, a user tends to lean one or both legs outwards. By monitoring gravity projection during a sitting period, one can estimate the leg on which TENS device 100 is placed. If the gravity projection along the x'-axis is positive for a majority of a sitting duration, then it is likely that TENS device 100 is placed on the right leg laterally. If gravity projection along x'-axis is negative for a majority of a sitting period, then it is likely that TENS device 100 is placed on the left leg medially.

Controller For Modifying Stimulation Parameters

The results of the activity, gait, and balance function assessments of the TENS user can be presented to the user or the caregivers of the user via smartphone 860 or similar connected devices. A more active lifestyle, steadier gait, and better balance are important examples of an improved quality of life and health. These improvements can be attributed to a reduction of pain as a result of TENS therapy. Changes in these functions are usually gradual and difficult to quantify. When the TENS users are provided with objective and background measurements of these important health metrics, they are more likely to continue with the TENS therapy.

A key feature of the present invention is that the novel TENS device automatically adjusts its stimulation parameters according to the aforementioned activity, gait, and balance measurements through controller unit 452 (FIGS. 4 and 12). When the TENS user experiences a reduction in daily activity levels and the reduction is associated with a reduced TENS therapy amount, the TENS device can be programmed to prompt the user or caregivers of the user to increase the TENS therapy amount via connected device 860. If the user enables the TENS device for an automatic increase of TENS therapy, the TENS device 100 can gradually increase the number of therapy sessions, individual therapy session duration, and/or therapeutic stimulation intensity.

Similarly, when gait or balance functions regress to lower levels, an increase in TENS therapy (in frequency, duration, and/or intensity) may increase the efficacy of its analgesic effect and improve gait and balance functions.

Knowledge of the limb and the rotational position of the TENS device placement allows automatic adjustment of therapeutic intensity levels used by the TENS device to deliver effective therapy. Depending upon the exact placement position of the TENS device on the body, optimal therapeutic stimulation intensity levels may be different. By automatically correlating preferred stimulation intensity levels with exact placement locations based on manual adjustments by the user in prior uses, the TENS device can adjust stimulation intensity automatically through machine learning once its placement location is estimated.

Exemplary Operation

In one preferred form of the invention, TENS device 100 comprises a stimulator 105 (FIG. 2), an on-skin detector 265 (FIG. 4), a device position detector 528 (FIG. 12), a controller 452 (FIG. 4) for modifying stimulation parameters, and a processor 515 (FIG. 4) for analyzing activity, gait, balance, and device position. TENS device 100 is preferably configured/programmed to operate in the manner shown in FIGS. 4 and 12, among others.

More particularly, when TENS device 100 is secured to the upper calf 140 of the user, on-skin detector 265 communicates with gyroscope 133 and/or accelerometer 132 to indicate that an on-skin session has started and data from gyroscope 133 and/or accelerometer 132 are processed to determine the user's activity, gait, and balance measurements. The data will also be used to determine the placement position (including the limb) of TENS device 100 on the user.

At the onset of an on-skin session, the orientation of TENS device 100 is set to assume an upright orientation by device orientation detector 512. Based on accelerometer y-axis data, device orientation detector 512 will update the device orientation to either a confirmed upright status or a confirmed upside-down status. The confirmed status (upright or upside-down) will then be persistent until the on-skin session ends. A confirmed upside-down device orientation will cause accelerometer values in x- and y-axis to reverse their signs. With the sign-reversal, the data stream from gyroscope 133 and/or accelerometer 132 can be processed in the same manner for either device orientation status.

Although the y-axis of accelerometer 132 (incorporated in the TENS device) is approximately along the same direction as gravity when the user is standing, the alignment may not be perfect. As a result, the static gravity projected on the y-axis may not be exactly the same as −1*g. Device vertical alignment unit 514 (FIG. 12) determines the exact alignment relationship between the y-axis and gravity, and alignment results are used to remove static gravity to obtain net activity acceleration for activity and gait analysis. The alignment results can be updated periodically during the on-skin session. In addition to alignment, device vertical alignment unit 514 (FIG. 12) also determines negative zero-crossing threshold 312 (FIG. 7) and positive zero-crossing threshold 314 (FIG. 7) to define a zero-activity region. The zero-activity region may be updated continuously during the on-skin session.

Filter operation 516 (FIG. 12) applies filters to the y-axis data by removing the static gravity component and smoothing out rapid changes near the zero-activity region. Filtered y-axis data are used to determine the user's activity levels and types. Filter operations such as low-pass filters to remove high-frequency noise can also be applied to x-axis and z-axis accelerometer data.

Leg swing is a critical and necessary component in walking and running. Swing event identification unit 518 (FIG. 12) identifies components in the acceleration or gyroscope data waveforms characteristic to leg swings. The timing of events like toe-off and heel strike associated with each leg swing is extracted from the waveform features.

Stride counter 520 (FIG. 12) counts the number of strides cumulatively within a specific time period (such as 24-hour period) and results are reported to the user either as a display on TENS device 100 or through a connected device 860 (FIG. 4) linked to the TENS device (such as a smartphone connected to the TENS device via Bluetooth).

Walk detector 522 (FIG. 12) determines whether the user is walking by monitoring timing patterns of detected swing events. Regular occurrences of swing events with occurrence intervals between one-half second and 2 seconds are indicative of a walking period. It should be noted that the occurrence interval can be adapted to determine jogging or running.

Gait analyzer 524 (FIG. 12) receives input from swing event identification 518 (stride duration defined as time difference between consecutive toe-off events), stride counter 520 (the number of strides in a walk segment), and walk detector 522 (walking status) to determine whether a sufficient number of strides have been accumulated to perform gait variability analysis. If a sufficient number of stride durations are collected and the stride duration sequence has a sufficient length without outliers, stride variability measures are calculated for the walk segment. One such measure is the coefficient of variation (CoV), defined as the standard deviation divided by the mean of the stride duration sequence (expressed as a percentage value).

Gait variability reporter 526 (FIG. 12) tracks stride variability measures for individual walk segments. For each 24-hour day, the distribution of stride variability measures is constructed. Characterization of stride variability measures, such as minimum, median, and maximum, are reported to the user. Stride variability measures can also be used by controller 452 to modify stimulation parameters in order to reduce gait variability.

Device position detector 528 (FIG. 12) determines the rotational position of TENS device 100 on leg 140. During a swing phase, detector 528 estimates the forward motion acceleration vector direction in the plane defined by the x- and z-axis of accelerometer 132 based on the x- and z-axis data. The rotational angle θ 402 (FIG. 11) is estimated based on the projection of the acceleration vector $A_F$ 404 (FIG. 11) onto the x- and z-axes. The rotational position angle θ 402 can be continuously refined as more measurement data became available. The total duration of the same device position across multiple on-skin sessions within a set period of time (such as a 24-hour day) can be used to inform the user to prevent skin irritation. This is because it is generally advisable to air-out the skin under the TENS device from time to time to minimize the risk of skin irritation. Device position can also be used to control stimulation parameters as the nerve sensitivity at different locations of upper calf may be different.

Sitting-standing classifier 530 (FIG. 12) determines whether the user is in standing state or in sitting state during the time period when the user is not in a walking state. Sitting-standing classifier 530 uses the device rotational angle information to map the x- and z-axis accelerometer data to a new coordinate system 408 (FIG. 11), with the x'-axis in the body's medial-lateral direction and z'-axis in the body's anterior-posterior direction. Acceleration data in x'-z' coordinate system 408 allows sitting-standing classifier 530 to sense small leg motions in either the medial-lateral direction or the anterior-posterior direction when the acceleration in the y-axis direction has no activity and uses the relative magnitude of acceleration along the x'- and z'-axis directions to determine the standing and sitting state.

Body sway estimator 532 (FIG. 12) is a part of the balance assessment system incorporated in TENS device 100. Under the standing condition, body sway estimator 532 quantifies body sway using metrics such as total sway length and standard deviation of acceleration along the x'- and z'-axis. Body sway estimator 532 can also compare the body sway metrics under conditions without and with electrical stimulation disturbance.

TUG (Timed Up and Go) estimator 534 (FIG. 12) is another component of the balance assessment system. TUG estimator 534 monitors the transition time from sitting to taking the first strike in a walking segment.

Limb classifier 552 (FIG. 12) determines on which limb TENS device 100 is disposed. Limb classifier 552 is activated when the user is in sitting state. Limb classifier 552 takes advantage of the fact that each lower leg is likely to lean outwards (laterally) more often when the user's feet are resting on the floor while the user is sitting. The limb determination and rotational angle information together provide precise location information of the TENS device on the user.

Modifications Of The Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A stimulation device for treating pain in a user:

a wearable component comprising a housing configured for removable attachment to an outer skin surface of a of a user;

an electrode disposed on, or within, the housing of the wearable component;

a motion sensor disposed on, or within, the housing of the wearable component and configured for detecting one or more motion parameters of the user;

an energy source disposed within the housing of the wearable component and coupled to the electrode and configured to generate a plurality of electrical impulses and to transmit the electrical impulses transcutaneously from the electrode through the outer skin surface of the user to a target nerve within the user, wherein the electrical impulses are sufficient to stimulate one or more sensory nerves within the user to reduce a level of pain within the user; and a controller coupled to the motion sensor and the energy source and configured to adjust a stimulation parameter of the electrical impulses based on the one or more motion parameters.

2. The device of claim 1, wherein the one or more motion parameters comprise a gait characteristic of the user.

3. The device of claim 2, wherein the gait characteristic of the user comprises a coefficient of variation of a sequence of stride durations of the user.

4. The device of claim 1, wherein the one or more motion parameters comprises a balance function of the user.

5. The device of claim 4, wherein the balance function of the user is measured by at least one parameter selected from the group consisting of: (i) body sway amplitude, (ii) body sway frequency, and (iii) body sway path distance.

6. The device of claim 1, wherein the one or more motion parameters comprise an activity level of a user.

7. The device of claim 6, wherein the activity level of the user comprises one or more of a number of strides taken by the use, an amount of time walked by the user and an average cadence of the user.

8. The device of claim 1, wherein the stimulation parameter comprises one of an amplitude, a pulse width and a pulse frequency of the electrical impulses.

9. The device of claim 1, wherein the electrical impulses are generated and transmitted according to a treatment regimen, wherein the stimulation parameter comprises a duration of the treatment regimen.

10. The device of claim 1, wherein the wearable component comprises a strap having a first end and a second end configured for removable coupling to the first end for removable attachment to a limb of the user.

11. A method for treating pain in a user:

contacting an outer skin surface of a user with an electrode;

attaching the electrode to the outer surface with a wearable component comprising a housing;

applying at least one electrical impulse to the electrode;

transmitting the electrical impulse through the outer skin surface to a target nerve within the user, wherein the electrical impulses are sufficient to stimulate one or more sensory nerves within the user to reduce a level of pain within the user;

detecting one or more motion parameters of the user with a sensor disposed on, or within, the housing of the wearable component; and adjusting a stimulation parameter of the electrical impulses based on the one or more motion parameters.

12. The method of claim 11, wherein the one or more motion parameters comprise a gait characteristic of the user.

13. The method of claim 11, wherein the gait characteristic of the user comprises a coefficient of variation of a sequence of stride durations of the user.

14. The method of claim 11, wherein the one or more motion parameters comprises a balance function of the user.

15. The method of claim 14, wherein the balance function of the user is measured by at least one parameter selected from the group consisting of: (i) body sway amplitude, (ii) body sway frequency, and (iii) body sway path distance.

16. The method of claim 15, wherein the one or more motion parameters comprise an activity level of a user.

17. The method of claim 16, wherein the activity level of the user comprises one or more of a number of strides taken by the use, an amount of time walked by the user and an average cadence of the user.

18. The method of claim 11, wherein the stimulation parameter comprises one of an amplitude, a pulse width and a pulse frequency of the electrical impulses.

19. The method of claim 11, wherein the electrical impulses are generated and transmitted according to a treatment regimen, wherein the stimulation parameter comprises a duration of the treatment regimen.

20. The method of claim 11, further comprising wrapping a strap around the calf and attaching a first end of the strap to a second end of the strap to contact the electrode to the outer skin surface.

* * * * *